United States Patent [19]
Owen et al.

[11] Patent Number: 5,521,156
[45] Date of Patent: May 28, 1996

[54] CYCLIC NEUROKININ A ANTAGONISTS

[75] Inventors: Thomas J. Owen; Elizabeth M. Kudlacz, both of Cincinnati, Ohio; Scott L. Harbeson, Cambridge, Mass.; Stephen H. Buck, Tuscon, Ariz.

[73] Assignee: Merrell Pharmaceuticals Inc., Cincinnati, Ohio

[21] Appl. No.: 191,571

[22] Filed: Feb. 3, 1994

[51] Int. Cl.$^6$ .............................. A61K 38/12; C07K 7/64
[52] U.S. Cl. .................................... 514/11; 514/9; 514/2; 530/317; 930/270
[58] Field of Search ..................... 514/11, 9, 2; 530/317; 930/270

[56] References Cited

U.S. PATENT DOCUMENTS 4,102,877  7/1978  Nutt ........................................ 530/317

FOREIGN PATENT DOCUMENTS

| | | |
|---|---|---|
| 0190946 | 2/1986 | European Pat. Off. . |
| 0401177 | 12/1990 | European Pat. Off. . |
| 0528312 | 8/1992 | European Pat. Off. . |
| 9202546 | 2/1992 | WIPO . |
| 9521187 | 8/1995 | WIPO . |

OTHER PUBLICATIONS

McKnight, et al., Brit. J. of Pharm, Proceedings Supplement 90:266P (Mar. 1987).
Suman–Chauhan, et al., Brit. J. of Pharm. Proceedings Supplement 95:747p (Dec. 1988).
Howarth, et al., British J. of Pharm. Proceedings Supplement 96:360P (Mar. 1989).
Rovero, et al., Peptides 10:593–595 (1989).
Hagiwara, D. et al., Studies on Neurokinin Antagonists 1. The Design of Novel Tripeptides Possessing the Glutaminyl–D–tryptophylphenylalanine Sequence as Substance P Antagonists, J. Med. Chem. 1992, 35, 2015–2025.
Hagiwara, D., et al., Studies on Neurokinin Antagonists. 2. Design and Structure–Activity Relationships of Novel Tripeptide Substance P Antagonists, N$^\alpha$–[N$^\alpha$–N$^\alpha$–Acetyl–L–threonyl)–N$^1$–formyl–D–tryptophyl]–N–methyl–N–(phenyl–mehtyl)–L–phenylalaninamide and its Related Compounds.
Ichinose, M., et al, Protection against bradykinin–induced bronchoconstriction in asthmatic patients by neurokinin receptor antagonist, The Lancet, vol. 340, Nov. 21, 1992.
Barnes, P. J., et al., TIPS Reviews, May 1990, vol. 11, Modulation of neurogenic inflammation: novel approaches to inflammatory disease.
Sasaki, et al., "Solid Phase Synthesis of Peptides Containing the CH$_2$NH Peptide Bond Isostere" Peptides, vol. 8, pp. 119–121 (1987).
McKnight, A. T., et al. Regulatory Peptides 22 (1–2):126 (Jul. 1988).
Fletcher, et al., Brit. J. Pharm, Proceedings Supplement 91:360P (Jun. 1987).
McElroy et al, J. Med. Chem., vol. 35, pp. 2582–2591, (1992).
Harbeson, Peptides, Proceedings of the 11th Am. Pept. Symp., pp. 180–181, (Jul. 9–14, 1989).
Harbeson, Peptides, Proceedings of the 12th Am. Pept. Symp., (Jun. 16–21, 1991), pp. 124–125.
Maggi, Br. J. Pharmacol., vol. 108, pp. 588–592, (1990).

*Primary Examiner*—Margaret Parr
*Assistant Examiner*—T. D. Wessendorf
*Attorney, Agent, or Firm*—William R. Boudreaux

[57] ABSTRACT

Antagonists of neurokinin A which are novel cyclic hexapeptide and octapeptide compounds are described. The antagonism is confirmed using conventional competitive binding and biochemical assays as well as conventional physiological tests and the use of these derivatives in a variety of conditions in which neurokinin A is implicated is also described.

27 Claims, 1 Drawing Sheet

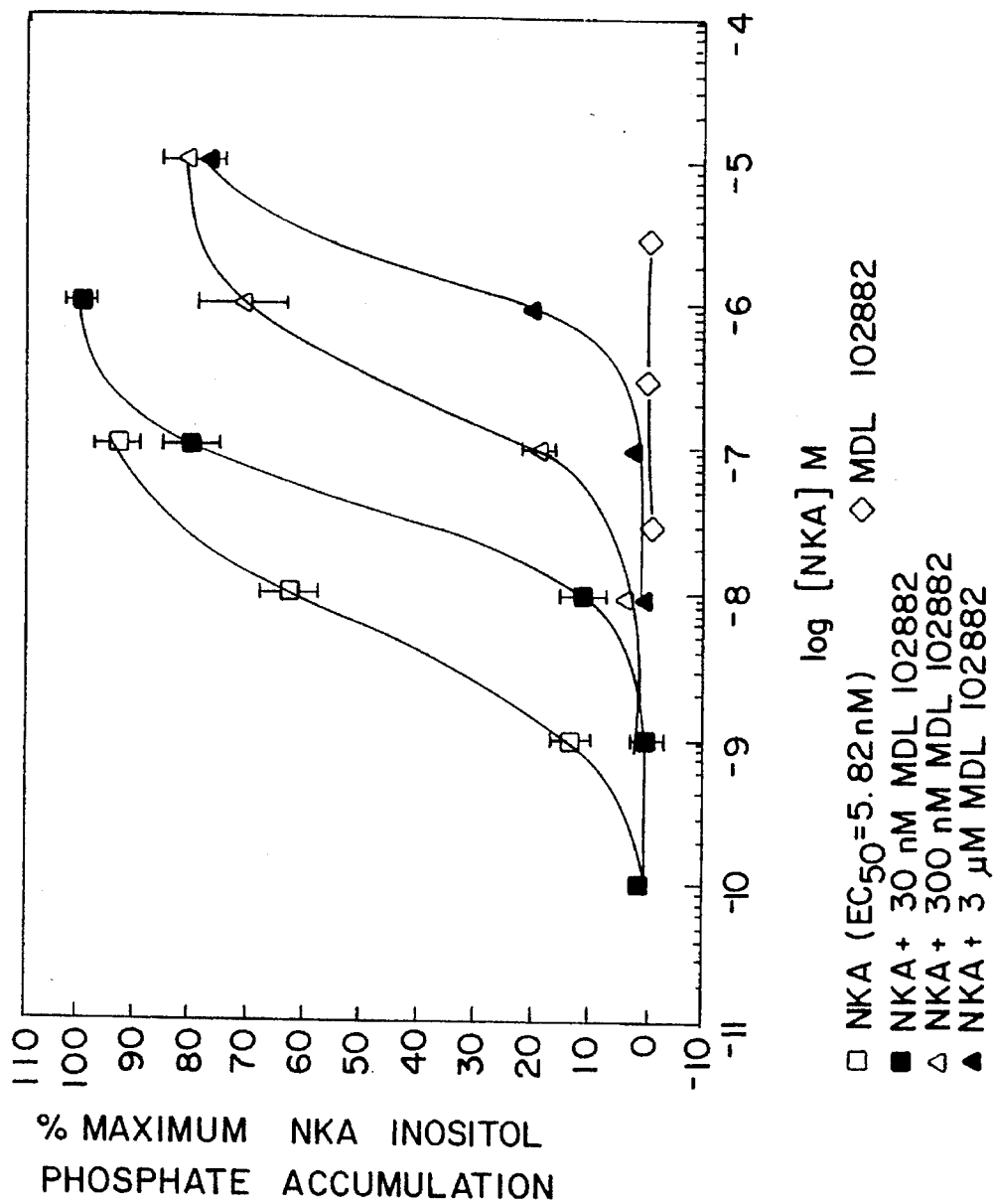

CYCLIC NEUROKININ A ANTAGONISTS

BACKGROUND OF THE INVENTION

The present invention relates to novel cyclic peptide compounds which are antagonists of neurokinin A and pharmaceutically acceptable salts thereof. It is an object of the present invention, therefore, to provide new and useful compounds and pharmaceutically acceptable salts thereof.

Neurokinin A and related tachykinins, substance P and neurokinin B, are a group of naturally occurring peptides shown to have a wide distribution within body tissue and produce a myriad of biological effects. Although there is evidence for a role for tachykinins in the central nervous system, the majority of their effects have been studied in peripheral tissues. For example, neurokinin A potently contracts airway smooth muscle while producing minor effects on mucus secretion, vasodilatation and microvascular leakage suggesting a primary utility of these compounds as novel anti-bronchoconstrictor agents. Other tissues in which neurokinin A has been shown to produce smooth muscle contraction includes iris sphincter, various parts of the gastrointestinal tract, vasculature, genitourinary system including ureter, renal pelvis and urinary bladder suggesting a use for tachykinin antagonists as antispastic agents.

A further object of the present invention is to provide compounds, or pharmaceutically acceptable salts thereof, for the treatment and prevention of various diseases in a patient in need thereof. Since it is also believed that tachykinins are involved in inflammation and immune functions, they are potentially useful in the treatment of conditions associated with inflammation, including asthma, allergies, bronchitis, rhinitis, Crohn's disease, ulcerative colitis, rheumatoid arthritis, osteoarthritis, migraine, cystitis and hypersensitivity reactions. Tachykinin antagonism may also be appropriate therapy for the treatment of cough, pain, peripheral neuropathy, post-herpetic neuralgia, adverse immunological reactions, emesis, blood flow disorders due to vasodilatation, ophthalmic diseases, such as conjunctivitis and cutaneous diseases such as contact dermatitis, atopic dermatitis, urticaria and the like. Various central nervous system disorders including anxiety, depression, psychosis, schizophrenia and dementia may also be amenable to treatment with tachykinin antagonists.

SUMMARY OF THE INVENTION

The present invention relates to compounds of formulae (1), (2), (3) and (4) and to their hydrates, stereoisomers, isosteres and pharmaceutically acceptable salts. Specifically, the compounds of Formula 1 comprise a cyclic hexapeptide of the formula:

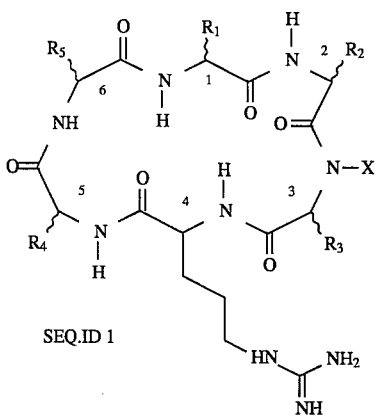

SEQ.ID 1

Formula 1 wherein $R_1$ is benzyl, p-hydroxybenzyl or 3-indolylmethyl;

$R_2$ is benzyl, 3-indolylmethyl or $(CH_2)_2$—$CONH_2$;

$R_3$ is a $C_{1-5}$ linear or branched alkyl and X is H or $R_3$ and X are joined together to form —$(CH_2)_3$—;

$R_4$ is H, benzyl, 3-indolylmethyl or p-hydroxybenzyl;

$R_5$ is H, methyl or 3-indolylmethyl;

with the proviso that when $R_2$ is —$(CH_2)_2$—$CONH_2$, $R_1$ is p-hydroxybenzyl and the carbon to which $R_1$ is attached is in an (R) absolute configuration;

or a hydrate, isostere or pharmaceutically acceptable salt thereof.

Also in accord with this invention, there are provided novel peptides of the formula

SEQ.ID 2

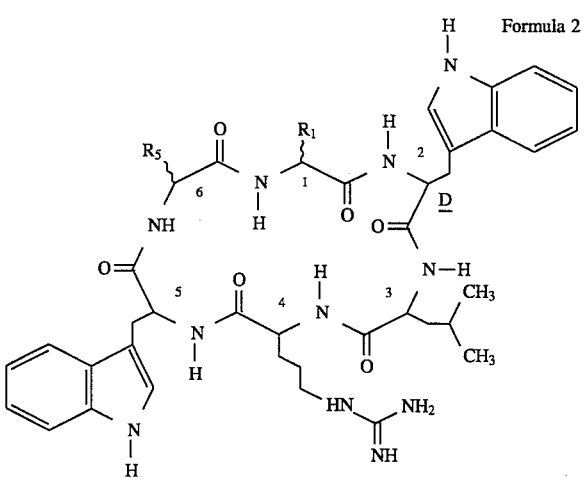

Formula 2 wherein $R_1$ is p-hydroxybenzyl or 3-indolylmethyl and $R_5$ is H or methyl;

or a hydrate, isostere or pharmaceutically acceptable salt thereof.

Similarly, there are provided novel peptides of the formula

Formula 3

SEQ.ID 3 wherein
- $B_1$ is a $C_{1-4}$ linear or branched alkyl, benzyl, p-hydroxybenzyl or 3-indolylmethyl;
- $B_2$ is $(CH_2)_4—NH_2$, $(CH_2)_3—NH_2$, $(CH_2)_3NHC(=NH)NH_2$ or 3-indolylmethyl;
- $B_3$ is p-hydroxybenzyl or 3-indolylmethyl;
- $B_4$ is H or $(CH_2)_2—CONH_2$;

or a hydrate, isostere or pharmaceutically acceptable salt thereof.

Likewise, there are provided novel peptides of the formula

Formula 4

SEQ.ID 4 wherein
- $R_1$ is p-hydroxybenzyl or 3-indolylmethyl;
- $R_5$ is H or methyl; and
- Q is p-chlorobenzyl, p-nitrobenzyl, p-$NH_2$-benzyl, p-methoxybenzyl, 3-indolylmethyl or is a group of the formulae X' is H;

wherein Q and X', along with the carbon and nitrogen to which they are respectively attached, can be attached to form a group of the formula or a hydrate, isostere or pharmaceutically acceptable salt thereof.

The present invention also provides a method for the treatment of a patient afflicted with a respiratory disease comprising administering to said patient a therapeutically effective amount of a compound of the formula Formula 5

SEQ.ID 5 wherein
- $R_1$ is benzyl, p-hydroxybenzyl or 3-indolylmethyl;
- $R_2$ is benzyl, 3-indolylmethyl or $(CH_2)_2—CONH_2$;
- $R_3$ is a $C_{1-5}$ linear or branched alkyl and X is H or $R_3$ and X are joined together to form —$(CH_2)_3$—;
- $R_4$ is H, benzyl, 3-indolylmethyl or p-hydroxybenzyl;
- W is H, methyl or 3-indolylmethyl and Z is H or W and Z are joined together to form —$(CH_2)_3$—;

with the proviso that when $R_2$ is $(CH_2)_2$—COOH, $R_1$ is p-hydroxybenzyl and the carbon to which $R_1$ is attached is in an (R) absolute configuration;

or a stereoisomer, isostere or pharmaceutically acceptable salt thereof.

In addition, the present invention provides a method for providing an analgesic effect in a patient in need thereof, comprising the administration thereto of a therapeutically effective analgesic amount of a compound of formulae (1), (2), (3), (4) or (5), or a stereoisomer, isostere or pharmaceutically acceptable salt thereof.

BRIEF DESCRIPTION OF THE DRAWINGS

FIG. 1 illustrates the ability of the cyclic peptide, cyclo [Tyr-trp-Leu-Arg-Trp-Gly] (MDL 102,882) to produce dose-related antagonism of NKA-induced phosphatidylinositol (PI) turnover in SKLKB82#3 cells. Data are expressed as percent stimulation of total inositol phosphate accumulation over basal levels and normalized to the maximum response produced by NKA. Data are MEAN±S.E.M. of values from four (4) separate experiments. Identity of each dose-response line is as listed below and in FIG. 1.

- —□— NKA($EC_{50}$=5.82nM)
- —■— NKA + 30nM cyclo[Tyr—trp—Leu—Arg—Trp—Gly]
- —△— NKA + 300nM cyclo[Tyr—trp—Leu—Arg—Trp—Gly]
- —▲— NKA + 3μM cyclo[Tyr—trp—Leu—Arg—Trp—Gly]
- —◊— cyclo[Tyr—trp—Leu—Arg—Trp—Gly]

DETAILED DESCRIPTION OF THE INVENTION

The term "$C_{1-5}$ linear or branched alkyl" when used in the instant application is intended to represent those alkyl groups either straight or branched chain, which have from 1–5 carbon atoms. Examples include methyl, ethyl, propyl, isopropyl, butyl, isobutyl, tert-butyl, pentyl, isopentyl, sec-pentyl, cyclopentyl and the like.

The term "stereoisomer" is a general term for all isomers of individual molecules that differ only in the orientation of their atoms in space. It includes mirror image isomers (enantiomers), geometric (cis/trans) isomers, and isomers of compounds with more than one chiral center that are not mirror images of one another (diastereo-isomers). For amino-acids, the designations D/L or R/S can be used as described in IUPAC-IUB Joint Commission on Biochemical Nomenclature, *Eur. J. Biochem.* 138: 9–37 (1984). The term "(R) absolute configuration" is meant to describe the carbon to which $R_1$ is attached in this context. The natural amino acids, with the exception of glycine, contain a chiral carbon atom. Unless otherwise specifically indicated, the preferred compounds are the optically active amino acids of the L-configuration; however, applicants contemplate that the amino acids of the formulae (1), (2), (3) or (4) compounds can be of either the D- or L-configurations or can be mixtures of the D- and L-isomers, including racemic mixtures. As used in this application, the designation

~~~ refers to a bond for which the stereochemistry is not designated. The designation "<u>D</u>" at amino acid position 2 of formulae (2) and (4) and at amino acid position 14 of formulae (3) is meant to convey that the amino acids present at those positions (with the exception being when those amino acids are glycine) are all in the "D" configuration. The recognized abbreviations for the α-amino acids are set forth in Table I.

TABLE I

| AMINO ACID | SYMBOL |
|---|---|
| Alanine | Ala |
| Glycine | Gly |
| Isoleucine | Ile |
| Leucine | Leu |
| Lysine | Lys |
| Phenylalanine | Phe |
| Arginine | Arg |
| Tyrosine | Tyr |
| Tryptophan | Trp |
| Valine | Val |
| Norvaline | Nva |
| Norleucine | Nle |
| Glutamic acid | Glu |
| Proline | Pro |
| Ornithine | Orn |
| p-Chlorophenylalanine | p-Cl-Phe |
| p-Nitrophenylalanine | p-$NO_2$-Phe |
| p-$NH_2$-Phenylalanine | p-$NH_2$-Phe |
| 1,2,3,4-tetrahydro-isoquinoline-7-hydroxy-3-carboxylic acid | Tiq(OH) |
| 1,2,3,4-tetrahydro-isoquinoline-3-carboxylic acid | Tiq |
| Naphthylalanine | Nal |
| Fluorenylglycine | Flg |
| Diphenylalanine | Dpa |

"Isostere" means the normal peptide bond between attached amino acids (—C(O)NH—) is in a modified form of —$CH_2$NH— (reduced), C(O)N($CH_3$) (N-methylamide), —COC$H_2$— (keto), —$CH_2$— (OH)C$H_2$— (hydroxy), —CH(N$H_2$)C$H_2$— (amino), —$CH_2CH_2$— (hydrocarbon), or is inverted (—HN(C═O)—). Preferably the compounds of the present invention are not in isosteric forms.

The compounds of formulae (1), (2), (3), (4) and (5) can form pharmaceutically acceptable salts with any non-toxic, organic or inorganic acid. Illustrative inorganic acids which form suitable salts include hydrochloric, hydrobromic, sulphuric and phophoric acid and acid metal salts such as sodium monohydrogen orthiophospate and potassium hydrogen sulfate. Illustrative organic acids which form suitable salts include the mono, di and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic, and sulfonic acids such as methane sulfonic acid and 2-hydroxyethane sulfonic acid.

Preferred embodiments of the subject compounds of the present invention are best realized in the compounds of formulae (1), (2), (3), (4) and (5) wherein:

$R_1$ is benzyl, p-hydroxybenzyl or 3-indolylmethyl; said $R_1$ values being derived from the D- or L-amino acids: phenylalanine, tyrosine and tryptophan, respectively;

$R_2$ is benzyl, 3-indolylmethyl, or $(CH_2)_2$—CON$H_2$; said $R_2$ values being derived from the D- or L-amino acids: phenylalanine, tryptophan or glutamine, respectively;

$R_3$ is $C_{1-5}$ linear or branched alkyl and X is H or $R_3$ and X are joined together to form —$(CH_2)_3$—; said $R_3$ values, or the value of $R_3$ and X in combination, being derived from the D- or L-amino acids: glycine, alanine, leucine, isoleucine, norleucine, valine, norvaline or proline, respectively;

$R_4$ is H, benzyl, 3-indolylmethyl, or p-hydroxybenzyl; said $R_4$ values being derived from the D- or L-amino acids: glycine, phenylalanine, tryptophan or tyrosine, respectively;

$R_5$ is H, methyl or 3-indolylmethyl; said $R_5$ values being derived from the D- or L-amino acids: glycine, alanine or tryptophan, respectively;

$B_1$ is $C_{1-5}$ linear or branched alkyl, benzyl, p-hydroxybenzyl or 3-indolylmethyl; said $B_1$ values being derived from the D- or L-amino acids: glycine, alanine, leucine, isoleucine, norleucine, valine, norvaline, phenylalanine, tyrosine or tryptophan, respectively;

$B_2$ is $(CH_2)_4$—$NH_2$, $(CH_2)_3$—$NH_2$, $(CH_2)_3$—$NHC(=NH)NH_2$ or 3-indolylmethyl; said $B_2$ values being derived from the D- or L-amino acids: lysine, ornithine, arginine or tryptophan, respectively;

$B_3$ is p-hydroxybenzyl or 3-indolylmethyl; said $B_3$ values being derived from the D- or L-amino acids: tyrosine or tryptophan, respectively;

$B_4$ is H or $(CH_2)_2$—$CONH_2$; said $B_4$ values being derived from the D- or L-amino acids: glycine or glutamine, respectively;

Q is p-chlorobenzyl, p-nitrobenzyl, p-$NH_2$-benzyl, p-methoxybenzyl, or is a group of the formulae

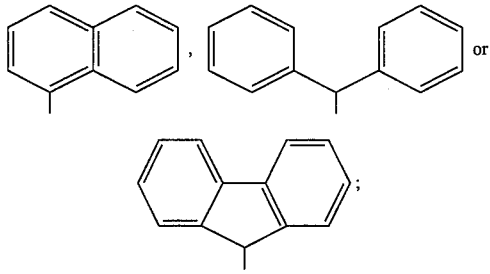

and X' is H; or wherein Q and X', along with the carbon and nitrogen to which they are respectively attached, can be attached to form a group of the formula

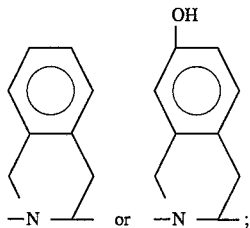

said Q values, or the value of Q and X' in combination, being derived from the D- or L-amino acids: p-chlorophenylalanine, p-nitrophenylalanine, p-$NH_2$-benzyl, methyltyrosine, naphthylalanine, fluorenylglycine, diphenylalanine, 1,2,3,4-tetrahydro-isoquinoline-3-carboxylic acid, or 1,2,3,4-tetrahydro-isoquinoline-7-hydroxy-3-carboxylic acid, respectively; and W is H, methyl or 3-indolylmethyl and Z is H or W and Z are joined together to form —$(CH_2)_3$—.

Preferred compounds of formula (1) are those wherein:
$R_1$ is p-hydroxybenzyl or 3-indolylmethyl;
$R_2$ is 3-indolylmethyl;
$R_3$ is $CH_2CH(CH_3)_2$ and X is H;
$R_4$ is 3-indolylmethyl;
$R_5$ is H or methyl.

Shorthand formats for expressing the preferred compounds of formula (1) include the structure: cyclo[$AA^1$-$AA^2$-$AA^3$-$AA^4$-$AA^5$-$AA^6$] or the cyclic structure:

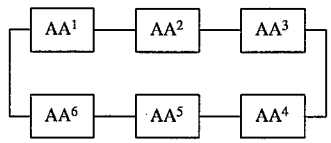

where $AA^1$–$AA^6$ are generic symbols for the amino acid residues described above giving rise to the $R_1$–$R_6$ radicals, respectively, as described for formula (1).

More preferred compounds of formula (1) are those wherein:
$R_1$ is p-hydroxybenzyl or 3-indolylmethyl;
$R_2$ is 3-indolylmethyl;
$R_3$ is $CH_2CH(CH_3)_2$ and X is H;
$R_4$ is 3-indolylmethyl;
$R_5$ is H.

The compounds of formula (2) are an even more preferred group of compounds of formula (1). Amino acids 2–5 all have fixed stereochemistry—amino acid 2 is in the (D) configuration while amino acids 3–5 are all in the (L) configuration. Shorthand formats for expressing the compounds of formula (2) include the structure: cyclo[$AA^1$-trp-Leu-Arg-Trp-$AA^6$] or the cyclic structure:

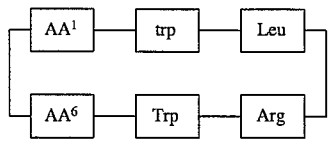

where trp is D-tryptophan, Leu is L-leucine, Arg is L-arginine, Trp is L-tryptophan and $AA^1$ and $AA^6$ are generic symbols for the amino acid residues described above giving rise to the $R_1$ and $R_6$ radicals, as described in formula (2).

Representative examples of the novel peptides of formulae (1) and (2), depicted here in abbreviated format include:
cyclo[Tyr-trp-Leu-Arg-Trp-Gly] SEQ. ID 6
cyclo[Trp-trp-Leu-Arg-Trp-Gly] SEQ. ID 7
cyclo[tyr-trp-Leu-Arg-Trp-Gly] SEQ. ID 8
cyclo[Tyr-trp-Leu-Arg-Tyr-Gly] SEQ. ID 9
cyclo[Tyr-trp-Leu-Arg-Trp-Ala] SEQ. ID 10
cyclo[Tyr-trp-Leu-Arg-Trp-ala] SEQ. ID 11
cyclo[Tyr-Trp-Leu-Arg-Trp-Gly] SEQ. ID 12
cyclo[Tyr-trp-Ala-Arg-Trp-Gly] SEQ. ID 13
cyclo[Tyr-trp-Leu-Arg-trp-Gly] SEQ. ID 14
cyclo[tyr-Gln-Leu-Arg-Trp-Gly] SEQ. ID 15
cyclo[Tyr-trp-Leu-Arg-Tyr-Ala] SEQ. ID 16
cyclo[Tyr-trp-Leu-Arg-Gly-Trp] SEQ. ID 17
cyclo[Tyr-trp-Pro-Arg-Trp-Gly] SEQ. ID 18
cyclo[Phe-phe-Pro-Arg-Phe-Gly]. SEQ. ID 19

Preferred compounds of formula (3) are those wherein: $B_1$ is $CH_2CH(CH_3)_2$ or p-hydroxybenzyl; $B_2$ is $(CH_2)_3$—$NHC(=NH)NH_2$ or 3-indolylmethyl.

The short-hand structure of the preferred compounds of formula (3) may be depicted as: cyclo[$AA^{11}$-$AA^{12}$-$AA^{13}$-$AA^{14}$-Leu-Arg-Trp-Gly] or the cyclic structure:

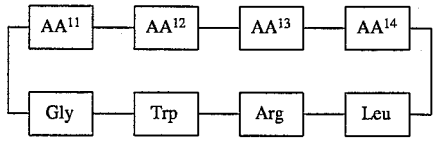

More preferred compounds of formula (3) include those wherein:

$B_1$ is $CH_2CH(CH_3)_2$;
$B_2$ is $(CH_2)_3$—$NHC(=NH)NH_2$;
$B_3$ is 3-indolylmethyl; and
$B_4$ is H; or
$B_1$ is p-hydroxybenzyl;
$B_2$ is 3-indolylmethyl;
$B_3$ is p-hydroxybenzyl; and
$B_4$ is $(CH_2)_2$—COOH.

Representative examples of the novel peptides of formula (3), depicted here in abbreviated format include:
cyclo[Leu-Arg-Trp-Gly-Leu-Arg-Trp-Gly] SEQ. ID 20
cyclo[Tyr-Trp-Tyr-glu-Leu-Arg-Trp-Gly] SEQ. ID 21

Preferred compounds of formula (4) are those wherein:
$R_1$ is p-hydroxybenzyl or 3-indolylmethyl;
$R_5$ is H or methyl;
X' is H
Q is p-chlorobenzyl, p-nitrobenzyl, p-$NH_2$-benzyl or is a group of the formula

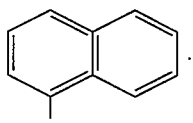

Representative examples of the novel peptides of formula (4), depicted here in abbreviated format include:
cyclo[Tyr-trp-Leu-Arg-Nal-Gly] SEQ. ID 22
cyclo[Tyr-trp-Leu-Arg-(p-NO2-Phe)-Gly] SEQ. ID 23
cyclo[Tyr-trp-Leu-Arg-(p-NH$_2$-Phe)-Gly] SEQ. ID 24
cyclo[Tyr-trp-Leu-Arg-(p-Cl-Phe)-Gly]. SEQ. ID 25

Preferred compounds of formula (5) are those wherein:
$R_1$ is p-hydroxybenzyl or 3-indolylmethyl;
$R_2$ is 3-indolylmethyl;
$R_3$ is $CH_2CH(CH_3)_2$ and X is H;
$R_4$ is 3-indolylmethyl;
W is H or methyl and Z is H or W and Z are joined together to form —$(CH_2)_3$—.

Shorthand formats for expressing the preferred compounds of formula (5) include the structure: cyclo[$AA^1$-$AA^2$-$AA^3$-$AA^4$-$AA^5$-$AA^6$] or the cyclic structure:

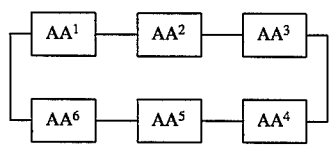

where $AA^1$–$AA^6$ are generic symbols for the amino acid residues described above giving rise to the $R_1$–$R_6$ radicals, respectively, as described for formula (5).

More preferred compounds of formula (5) are those wherein:
$R_1$ is p-hydroxybenzyl or 3-indolylmethyl;
$R_2$ is 3-indolylmethyl;
$R_3$ is $CH_2CH(CH_3)_2$ and X is H;
$R_4$ is 3-indolylmethyl;
$R_5$ is H.

Representative examples of the peptides of formula (5), depicted here in abbreviated format include:
cyclo[Tyr-trp-Leu-Arg-Trp-Gly], SEQ. ID 6
cyclo[Trp-trp-Leu-Arg-Trp-Gly], SEQ. ID 7
cyclo[tyr-trp-Leu-Arg-Trp-Gly], SEQ. ID 8
cyclo[Tyr-trp-Leu-Arg-Tyr-Gly], SEQ. ID 9
cyclo[Tyr-trp-Leu-Arg-Trp-Ala], SEQ. ID 10
cyclo[Tyr-trp-Leu-Arg-Trp-ala], SEQ. ID 11
cyclo[Tyr-Trp-Leu-Arg-Trp-Gly], SEQ. ID 12
cyclo[Tyr-trp-Ala-Arg-Trp-Gly], SEQ. ID 13
cyclo[Tyr-trp-Leu-Arg-trp-Gly] or SEQ. ID 14
cyclo[Tyr-trp-Leu-Arg-Trp-Pro]. SEQ. ID 26

In general, the compounds of formulae (1)–(5) may be prepared by cyclizing the corresponding linear peptides which are prepared by standard chemical reactions analogously known in the art. Scheme A outlines a general synthetic sheme for preparing the cyclic hexapeptides of formulae (1), (2), (4) and (5), but the cyclic octapeptides of formula (3) may also be made according to this scheme.

Scheme A

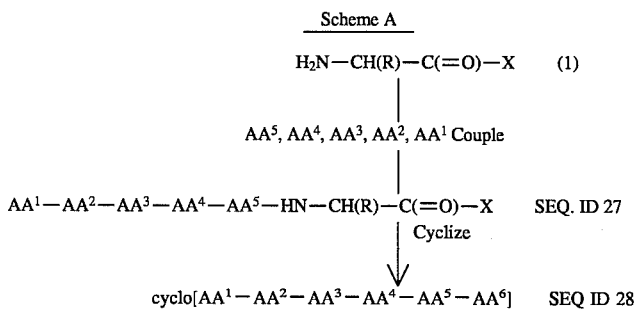

Scheme A provides a general synthetic scheme for preparing the compounds of formulae (1)–(5).

The $AA^1$, $AA^2$, $AA^3$, $AA^4$ and $AA^5$ groups can be linked to the free amino group of the amino acid derivative of structure (1). The $AA^1$, $AA^2$, $AA^3$, $AA^4$ and $AA^5$ groups can be linked to the unprotected, free amino compound by well known peptide coupling techniques. The so-linked linear peptide may then be cyclized by well known peptide cyclizing techniques.

Generally, peptides are elongated by deprotecting the α-amine of the C-terminal residue and coupling the next suitably protected amino acid through a peptide linkage using the methods described. This deprotection and coupling procedure is repeated until the desired sequence is obtained. This coupling can be performed with the constituent amino acids in stepwise fashion, as depicted in Scheme A, or by condensation of fragments (two to several amino acids), or combination of both processes, or by solid phase peptide synthesis according to the method originally described by Merrifield, *J. Am. Chem. Soc.*, 1963, 85, 2149–2154, the disclosure of which is hereby incorporated by reference. When a solid phase synthetic approach is employed, the C-terminal carboxylic acid is attached to an insoluble carrier (usually polystyrene). These insoluble carriers contain a group which will react with the α-carboxyl group group to form a bond which is stable to the elongation conditions but readily cleaved later. Examples of which are, but are not limited to: chloro- or bromomethyl resin, hydroxymethyl resin, and aminomethyl resin. Many of these resins are commercially available with the desired C-terminal amino acid already incorporated. Many of the suitably protected amino acids used in the present invention are available commercially. While the amino acids diphenylglycine and fluorenylglycine are not yet available commercially, they may be synthesized by art-known methods, for example, Chassaing, Josien, Lavielle, "Proceedings of the Eleventh American Peptide Symposium" and Martin J. O'Donnell and Robin L. Polt, *J. Org. Chem.*, 1982, 47, 2663–2666.

Alternatively, compounds of the invention can be synthesized using automated peptide synthesizing equipment. In addition to the foregoing, peptide synthesis are described in Stewart and Young, "Solid Phase Peptide Synthesis", 2nd ed., Pierce Chemical Co., Rockford, Ill. (1984); Gross, Meienhofer, Udenfriend, Eds., "The Peptides: Analysis, Synthesis, Biology", Vol 1, 2, 3, 5 and 9, Academic Press, New York, 1980–1987; Bodanszky, "Peptide Chemistry: A Practical Textbook", Springer-Verlag, New York (1988); and Bodanszky, et al. "The Practice of Peptide Synthesis" Springer-Verlag, New York (1984), the disclosures of which are hereby incorporated by reference.

Coupling between two amino acids, an amino acid and a peptide, or two peptide fragments can be carried out using standard coupling procedures such as the azide method, mixed carbonic acid anhydride (isobutyl chloroformate) method, carbodiimide (dicyclohexylcarbodiimide, diisopropylcarbodiimide, or water-soluble carbodiimide) method, active ester (p-nitrophenyl ester, N-hydroxy-succinic imido ester) method, Woodward reagent K method, carbonyldiimidazole method, phosphorus reagents such as BOP-Cl, or oxidation-reduction methods. Some of these methods (especially the carbodiimide method) can be enhanced by adding 1-hydroxybenzotriazole. These coupling reactions can be performed in either solution (liquid phase) or solid phase.

The functional groups of the constituent amino acids must be protected during the coupling reactions to avoid formation of undesired bonds. The protecting groups that can be used are listed in Greene, "Protective Groups in Organic Chemistry", John Wiley & Sons, New York (1981) and "The Peptides: Analysis, Synthesis, Biology", Vol. 3, Academic Press, New York (1981), the disclosure of which is hereby incorporated by reference.

The $\alpha$-carboxyl group of the C-terminal residue is usually protected by an ester that can be cleaved to give the carboxylic acid. Protecting groups which can be used include: 1) alkyl esters such as methyl and t-butyl, 2) aryl esters such as benzyl and substituted benzyl, or 3) esters which can be cleaved by mild base treatment or mild reductive means such as trichloroethyl and phenacyl esters.

The $\alpha$-amino group of each amino acid must be protected. Any protecting group known in the art can be used. Examples of which include: 1) acyl types such as formyl, trifluoroacetyl, phthalyl, and p-toluenesulfonyl; 2) aromatic carbamate types such as benzyloxycarbonyl (Cbz or Z) and substituted benzyloxycarbonyls, 1-(p-biphenyl)-1-methylethoxy-carbonyl, and 9-fluorenylmethyloxycarbonyl (Fmoc); 3) aliphatic carbamate types such as tertbutyloxycarbonyl (Boc), ethoxycarbonyl, diisopropylmethoxycarbonyl, and allyloxycarbonyl; 4) cyclic alkyl carbamate types such as cyclopentyloxycarbonyl and adamantyloxycarbonyl;; 5) alkyl types such as triphenylmethyl and benzyl; 6) trialkylsilane such as trimethylsilane; and 7) thiol containing types such as phenylthiocarbonyl and dithiasuccinoyl. The preferred $\alpha$-amino protecting group is either Boc or Fmoc, preferably Fmoc. Many amino acid derivatives suitably protected for peptide synthesis are commercially available.

The $\alpha$-amino protecting group is cleaved prior to the coupling of the next amino acid. When the Boc group is used, the methods of choice are trifluoroacetic acid, neat or in dichloromethane, or HCl in dioxane. The resulting ammonium salt is then neutralized either prior to the coupling or in situ with basic solutions such as aqueous buffers, or tertiary amines in dichloromethane or dimethylformamide. When the Fmoc group is used, the reagents of choice are piperidine or substituted piperidine in dimethylformamide, but any secondary amine or aqueous basic solutions can be used. The deprotection is carried out at a temperature between 0° C. and room temperature.

Any of the amino acid bearing side chain functionalities must be protected during the preparation of the peptide using any of the above-described groups. Those skilled in the art will appreciate that the selection and use of appropriate protecting groups for these side chain functionalities depends upon the amino acid and presence of other protecting groups in the peptide. The selection of such protecting groups is important in that it must not be removed during the deprotection and coupling of the $\alpha$-amino group. For example, when Boc is used as the $\alpha$-amino protecting group, p-toluenesulfonyl (tosyl) moieties can be used to protect the amino side chains of amino acids such as Lys and Arg. When Fmoc is chosen for the $\alpha$-amine protection usually tert-butyl based protecting groups are acceptable. For instance, Boc can be used for arginine.

Once the elongation of the peptide is completed all of the protecting groups are removed. When a solution phase synthesis is used, the protecting groups are removed in whatever manner is dictated by the choice of protecting groups. These procedures are well known to those skilled in the art.

When a solid phase synthesis is used, the peptide is cleaved from the resin usually simultaneously with the protecting group removal. When the Boc protection scheme is used in the synthesis, treatment with anhydrous HF containing additives such as dimethyl sulfide, anisole, thioanisole, or p-cresol at 0° C. is the preferred method for cleaving the peptide from the resin. The cleavage of the peptide can also be accomplished by other acidic reagents such as trifluoromethanesulfonic acid/trifluoroacetic acid mixtures. If the Fmoc protection scheme is used the N-terminal Fmoc group is cleaved with reagents described earlier. The other protecting groups and the peptide are cleaved from the resin using a solution of trifluoroacetic acid and various additives such as anisole, etc.

Subsequent to removal of the linear peptide from the resin and removal of any protecting groups as desirable, the linear peptide is cyclized using conventional procedures such as by treatment with triethylamine and diphenylphosphorylazide in dimethylformamide. Prior to purification of the crude cyclic peptide in the usual manner such as by use of chromatography, any remaining protecting and functional group precursors are removed or transformed into the desired group.

The following examples present typical syntheses. These examples are understood to be illustrative only and are not intended to limit the scope of the present invention in any way. As used herein, the following terms have the indicated meanings: "g" refers to grams; "mmol" refers to millimoles; "mL" refers to milliliters; "bp" refers to boiling point; "°C." refers to degrees Celsius; "mm Hg" refers to millimeters of mercury; "$\mu$L" refers to microliters; "$\mu$g" refers to micrograms; "$\mu$M" refers to micromolar; "BrZ" refers to bromobenzyloxycarbonyl; "Tos" refers to p-toluenesulfonyl; "Bzl" refers to benzyl; "NMP" refers to N-methylpyrolidinone; "HOBt" refers to 1-Hydroxybenzotriazole; "DCC" refers to N,N-dicyclohexylcarbodiimide; "DCM" refers to dichloromethane; "DMF" refers to dimethylformamide; "DPPA" refers to diphenylphosphorylazide; "TEA" refers to triethylamine.

EXAMPLE 1

Preparation of cyclo[Tyr-trp-Leu-Arg-Trp-Gly]
SEQ. ID 6

A. Synthesis of the Linear Peptide

The peptide of Example 1 is synthesized by standard solid phase methods using an Applied Biosystems 430A automated peptide synthesizer and protocols supplied by the manufacturer. Commercially available Boc-amino acids are used with the following side chain protection: Tyr(BrZ), Arg(Tos), Glu(Bzl). Commercially available Boc-Gly-PAM resin (0.5 mmol, Applied Biosystems) is deprotected with trifluoroacetic acid (2% anisole) and coupled in NMP with the HOBt esters of Boc-amino acids (4 equivalents). The HOBt esters of Boc-amino acids are formed by the reaction of the Boc-amino acid with DCC and HOBt. Couplings are carried out for 30 minutes and the resin is subsequently washed with NMP and DCM. Any unreacted amine is acylated with acetic anhydride. The deprotection and coupling are repeated until complete assembly of the protected peptide resin is achieved. The linear peptide is simultaneously deprotected and removed from the resin with anhydrous hydrogen fluoride (10 ml) at 0° C. for 30 minutes in the presence of anisole (5%). The peptide is extracted with 50% acetic acid, water and aqueous acetonitrile, and lyophilized.

B. Cyclization of the Linear Peptide

The crude linear peptide is dissolved in DMF (~5 μmol/ml) and cyclized with DPPA (5 equivalents) TEA to adjust the pH to 9. After completion of the reaction (4–48 hours), the solvent is removed and the crude cyclic peptide is lyophilized from acetonitrile/water. The cyclic peptide is desalted by gel filtration in 70% acetic acid over a Spectragel GF05 column (2.5×55 cm), and purified by reversed phase preparative HPLC (Dynamax $C_{18}$, 21.4×250 mm, Rainin) using various gradients of 0.1% aqueous TFA and acetonitrile. The purified peptide is characterized by Analytical HPLC (Vydac 218TP54, 4.6×250 mm), FAB-MS, and amino acid analysis.

Mol Wt: 861.4
AAA: Tyr 0.95(1); Leu 0.99(1); Arg 1.01(1); Gly 1.05(1).
FAB-MS: 862.4

Examples 2–29 are synthesized by the same or similar process to that of Example 1:

EXAMPLE 2

Preparation of cyclo[Trp-trp-Leu-Arg-Trp-Gly]
SEQ. ID 7

Mol Wt: 884.4
AAA: Leu 0.96(1); Arg 0.99(1); Gly 1.05(1).
FAB-MS: 885.4

EXAMPLE 3

Preparation of cyclo[tyr-trp-Leu-Arg-Trp-Gly] SEQ. ID 8

Mol Wt: 861.4
AAA: Tyr 1.00(1); Leu 0.95(1); Arg 1.00(1); Gly 1.05(1).
FAB-MS: 862.3

EXAMPLE 4

Preparation of cyclo[Tyr-trp-Leu-Arg-Tyr-Gly]
SEQ. ID 9

Mol Wt: 838.4
AAA: Tyr 1.91(2); Leu 0.91(1); Arg 1.01(1); Gly 1.17(1).
FAB-MS: 839.4

EXAMPLE 5

Preparation of cyclo[Tyr-trp-Leu-Arg-Trp-Ala]
SEQ. ID 10

Mol Wt: 875.4
AAA: Tyr 0.96(1); Leu 0.94(1); Arg 1.05(1); Ala 1.05(1).
FAB-MS: 876.3

EXAMPLE 6

Preparation of cyclo[Tyr-trp-Leu-Arg-Trp-ala] SEQ. ID 11

Mol Wt: 875.4
AAA: Tyr 0.97(1); Leu 0.95(1); Arg 1.03(1); Ala 1.04(1).
FAB-MS: 876.3

EXAMPLE 7

Preparation of cyclo[Tyr-Trp-Leu-Arg-Trp-Gly]
SEQ. ID 12

Mol Wt: 861.4
AAA: Tyr 0.97(1); Leu 0.99(1); Arg 0.98(1); Gly 1.07(1).
FAB-MS: 862.4

EXAMPLE 8

Preparation of cyclo[Tyr-trp-Ala-Arg-Trp-Gly]
SEQ. ID 13

Mol Wt: 819.4
AAA: Tyr 0.95(1); Arg 0.99(1); Gly 1.05(1); Ala 1.02(1).
FAB-MS: 820.4

EXAMPLE 9

Preparation of cyclo[Tyr-trp-Leu-Arg-trp-Gly] SEQ, ID 14

Mol Wt: 861.4
AAA: Tyr 0.96(1); Leu 0.99(1); Arg 1.00(1); Gly 1.06(1).
FAB-MS: 862.3

EXAMPLE 10

Preparation of cyclo[tyr-Gln-Leu-Arg-Trp-Gly]
SEQ. ID 15

Mol Wt: 803.4
AAA: Tyr 0.95(1); Leu 1.01(1); Arg 0.92(1); Gly 1,07(1); Glx 1.04(1).
FAB-MS: 804.5

EXAMPLE 11

Preparation of cyclo[Tyr-trp-Leu-Arg-Tyr-Ala]
SEQ. ID 16

Mol Wt: 852.4
AAA: Tyr 1.98(2); Leu 0.96(1); Arg 1.05(1); Ala 1.01(1).
FAB-MS: 853.4

EXAMPLE 12

Preparation of cyclo[Tyr-trp-Leu-Arg-Gly-Trp]
SEQ. ID 17

Mol Wt: 861.4
AAA: Tyr 0.83(1); Leu 0.89(1); Arg 1.10(1); Gly 1.19(1).
FAB-MS: 862.3

EXAMPLE 13

Preparation of cyclo[Tyr-trp-Pro-Arg-Trp-Gly]
SEQ. ID 18

Mol Wt: 845.4
AAA: Tyr 0.90(1); Arg 1.01(1); Gly 1.10(1); Pro 0.98 (1).
FAB-MS: 846.3

EXAMPLE 14

Preparation of cyclo[Phe-phe-Pro-Arg-Phe-Gly]
SEQ. ID 19

Mol Wt: 751.4
AAA: Arg 1.03(1); Gly 1.12(1); Pro 1.02(1); Phe 2.82(3).
FAB-MS: 752.3

EXAMPLE 15

Preparation of
cyclo[Leu-Arg-Trp-Gly-Leu-Arg-Trp-Gly] SEQ. ID
20

Mol Wt: 1024.6
AAA: Leu 2.00(2); Arg 1.90(2); Gly 2.10(2).
FAB-MS: 1025.4

EXAMPLE 16

Preparation of
cyclo[Tyr-Trp-Tyr-glu-Leu-Arg-Trp-Gly-] SEQ. ID
21

Mol Wt: 1152.5
AAA: Tyr 1.94(2); Leu 1.00(1); Arg 0.97(1); Gly 1.03(1); Glx (1).
FAB-MS: 1153.5

EXAMPLE 17

Preparation of cyclo[Tyr-Trp-Leu-Arg-Nal-Gly-]
SEQ. ID 22

Mol Wt: 872.5
AAA: Tyr 0.94(1); Leu 0.98(1); Arg 1.01(1); Gly 1.08 (1).
FAB-MS: 873.4

EXAMPLE 18

Preparation of
cyclo[Tyr-trp-Leu-Arg-(p-$NO_2$-Phe)-Gly] SEQ. ID
23

Mol Wt: 867.4
AAA: Tyr 0.95(1); Leu 0.97(1); Arg 1.02(1); Gly 1.08(1).
FAB-MS: 868.4

EXAMPLE 19

Preparation of
cyclo[Tyr-trp-Leu-Arg-(p-$NH_2$-Phe)-Gly] SEQ. ID
24

Mol Wt: 837.4
AAA: Tyr 0.97(1); Leu 0.98(1); Arg 1.00(1); Gly 1.06 (1).
FAB-MS: 838.4

EXAMPLE 20

Preparation of
cyclo[Tyr-trp-Leu-Arg-(p-Cl-Phe)-Gly] SEQ. ID 25

Mol Wt: 857.4
AAA: Tyr 0.97(1); Leu 0.98(1); Arg 1.00(1); Gly 1.05(1).
FAB-MS: 857.3

EXAMPLE 21

Preparation of cyclo[Tyr-trp-Leu-Arg-(Flg)-Gly](I)
SEQ. ID 29

Mol Wt: 896.5
AAA: Tyr 0.96(1); Leu 0.99(1); Gly 1.06(1).
FAB-MS: 897.5

EXAMPLE 22

Preparation of cyclo[Tyr-trp-Leu-Arg-(Flg)-Gly](II)
SEQ. ID 30

Mol Wt: 896.5
AAA: Tyr 0.94(1); Leu 1.01(1); Gly 1.06(1).
FAB-MS: 897.5

EXAMPLE 23

Preparation of cyclo[Tyr-trp-Leu-Arg-(Dpa)-Gly](I)
SEQ. ID 31

Mol Wt: 898.5
AAA: Tyr 0.97(1); Leu 1.04(1); Gly 1.00(1).
FAB-MS: 899.5

EXAMPLE 24

Preparation of cyclo[Tyr-trp-Leu-Arg-(Dpa)-Gly](II)
SEQ. ID 32

Mol Wt: 898.5
AAA: Tyr 1.00(1); Leu 1.04(1); Gly 0.97(1).
FAB-MS: 899.4

EXAMPLE 25

Preparation of
cyclo[Tyr-trp-Leu-Arg-(Me-Tyr)-Gly] SEQ. ID 33

Mol Wt: 852.4
AAA: Leu 0.97(1); Arg 0.99(1); Gly 1.04(1).
FAB-MS: 853.4

EXAMPLE 26

Preparation of cyclo[Tyr-trp-Leu-Arg-(Tig)-Gly]
SEQ. ID 34

Mol Wt: 834.4
AAA: Tyr 0.96(1); Leu 0.98(1); Arg 1.00(1); Gly 1.06(1).
FAB-MS: 835.5

EXAMPLE 27

Preparation of cyclo[Tyr-trp-Leu-Arg-(tig)-Gly]
SEQ. ID 35

Mol Wt: 834.4
AAA: Tyr 0.91(1); Leu 0.96(1); Arg 1.03(1); Gly 1.10(1).
FAB-MS: 835.5

EXAMPLE 28

Preparation of
cyclo[Tyr-trp-Leu-Arg-(Tig-OH)-Gly] SEQ. ID 36

Mol Wt: 850.4
AAA: Tyr 0.85(1); Leu 0.97(1); Arg 1.00(1); Gly 1.18(1).
FAB-MS: 851.4

EXAMPLE 29

Preparation of cyclo[Tyr-trp-Leu-Arg-Trp-Pro]
SEQ. ID 26

Mol Wt: 901.5
AAA: Tyr 0.94(1); Leu 0.94(1); Arg 1.07(1); Pro 1.04(1).
FAB-MS: 902.5

In a further embodiment, the present invention provides a method for the treatment of a patient afflicted with a respiratory disease comprising the administration thereto of a therapeutically effective amount of a compound of formulae (1), (2), (3), (4) or (5). The term "respiratory disease" refers to diseases or conditions characterized by bronchoconstriction and mucus hypersecretion. Respiratory diseases for which treatment with a compound of formulae (1), (2), (3), (4) or (5) will be particularly useful include: asthma, bronchitis, rhinitis, cough, and expectoration. Compounds of formulae (1), (2), (3), (4) or (5) which are particularly p referred for the treatment of respiratory diseases include:
cyclo[Tyr-trp-Leu-Arg-Trp-Gly] SEQ. ID 6
cyclo[Trp-trp-Leu-Arg-Trp-Gly] SEQ. ID 7
cyclo[tyr-trp-Leu-Arg-Trp-Gly] SEQ. ID 8
cyclo[Tyr-trp-Leu-Arg-Tyr-Gly] SEQ. ID 9
cyclo[Tyr-trp-Leu-Arg-Trp-Ala] SEQ. ID 10
cyclo[Tyr-trp-Leu-Arg-Trp-ala] SEQ. ID 11
cyclo[Tyr-Trp-Leu-Arg-Trp-Gly] SEQ. ID 12
cyclo[Tyr-trp-Ala-Arg-Trp-Gly] SEQ. ID 13
cyclo[Tyr-trp-Leu-Arg-trp-Gly] SEQ. ID 14
cyclo[tyr-Gln-Leu-Arg-Trp-Gly] SEQ. ID 15
cyclo[Tyr-trp-Leu-Arg-Tyr-Ala] SEQ. ID 16
cyclo[Tyr-trp-Leu-Arg-Gly-Trp] SEQ. ID 17
cyclo[Tyr-trp-Pro-Arg-Trp-Gly] SEQ. ID 18
cyclo[Phe-phe-Pro-Arg-Phe-Gly] SEQ. ID 19
cyclo[Leu-Arg-Trp-Gly-Leu-Arg-Trp-Gly] SEQ. ID 20
cyclo[Tyr-Trp-Tyr-glu-Leu-Arg-Trp-Gly] SEQ. ID 21
cyclo[Tyr-trp-Leu-Arg-Nal-Gly] SEQ. ID 22
cyclo[Tyr-trp-Leu-Arg-(p-$NO_2$-Phe)-Gly] SEQ. ID 23
cyclo[Tyr-trp-Leu-Arg-(p-$NH_2$-Phe)-Gly] SEQ. ID 24
cyclo[Tyr-trp-Leu-Arg-(p-$C_1$-Phe)-Gly] SEQ. ID 25
cyclo[Tyr-trp-Leu-Arg-Trp-Pro]. SEQ. ID 26

The term "therapeutically effective amount" refers to an amount which is effective, upon single or multiple dose administration to the patient, in providing relief of symptoms associated with respiratory diseases. As used herein, "relief of symptoms" of a respiratory disease refers to a decrease in severity over that expected in the absence of treatment and does not necessarily indicate a total elimination or cure of the disease. In determining the therapeutically effective amount or dose, a number of factors are considered by the attending diagnostician, including, but not limited to: the species of mammal; its size, age, and general health; the specific disease involved; the degree of or involvement or the severity of the disease; the response of the individual patient; the particular compound administered; the mode of administration; the bioavailability characteristics of the preparation administered; the dose regimen selected; the use of concomitant medication; and other relevant circumstances.

A therapeutically effective amount of a compound of formulae (1), (2), (3), (4) or (5) is expected to vary from about 0.1 milligram per kilogram of body weight per day (mg/kg/day) to about 100 mg/kg/day. Preferred amounts are expected to vary from about 0.5 to about 10 mg/kg/day.

In addition, the present invention provides a method for providing an analgesic effect in a patient in need thereof, comprising the administration thereto of a therapeutically effective analgesic amount of a compound of formulae (1), (2), (3), (4) or (5). A patient is in need of an analgesic effect when a patient is suffering from acute or chronic pain. The identification of those patients who are in need of an analgesic effect is well within the ability and knowledge of one skilled in the art. Compounds of formulae (1), (2), (3), (4) or (5) which are particularly preferred for providing an analgesic effect include:
cyclo[Tyr-trp-Leu-Arg-Trp-Gly] SEQ. ID 6
cyclo[Trp-trp-Leu-Arg-Trp-Gly] SEQ. ID 7
cyclo[tyr-trp-Leu-Arg-Trp-Gly] SEQ. ID 8
cyclo[Tyr-trp-Leu-Arg-Tyr-Gly] SEQ. ID 9
cyclo[Tyr-trp-Leu-Arg-Trp-Ala] SEQ. ID 10
cyclo[Tyr-trp-Leu-Arg-Trp-ala] SEQ. ID 11
cyclo[Tyr-Trp-Leu-Arg-Trp-Gly] SEQ. ID 12
cyclo[Tyr-trp-Ala-Arg-Trp-Gly] SEQ. ID 13
cyclo[Tyr-trp-Leu-Arg-trp-Gly] SEQ. ID 14
cyclo[tyr-Gln-Leu-Arg-Trp-Gly] SEQ. ID 15
cyclo[Tyr-trp-Leu-Arg-Tyr-Ala] SEQ. ID 16
cyclo[Tyr-trp-Leu-Arg-Gly-Trp] SEQ. ID 17
cyclo[Tyr-trp-Pro-Arg-Trp-Gly] SEQ. ID 18
cyclo[Phe-phe-Pro-Arg-Phe-Gly] SEQ. ID 19
cyclo[Leu-Arg-Trp-Gly-Leu-Arg-Trp-Gly] SEQ. ID 20
cyclo[Tyr-Trp-Tyr-glu-Leu-Arg-Trp-Gly] SEQ. ID 21
cyclo[Tyr-trp-Leu-Arg-Nal-Gly] SEQ. ID 22
cyclo[Tyr-trp-Leu-Arg-(p-$NO_2$-Phe)-Gly] SEQ. ID 23
cyclo[Tyr-trp-Leu-Arg-(p-$NH_2$-Phe)-Gly] SEQ. ID 24
cyclo[Tyr-trp-Leu-Arg-(p-Cl-Phe)-Gly] SEQ. ID 25
cyclo[Tyr-trp-Leu-Arg-Trp-Pro]. SEQ. ID 26

The term "therapeutically effective analgesic amount" refers to an amount which is effective, upon single or multiple dose administration to the patient, in providing an analgesic effect. As used herein, "analgesic effect" as used herein refers to a decrease in severity of pain over that expected in the absence of treatment and does not necessarily indicate a total elimination or relief of pain. Successful treatment is also understood to include prophylaxis in treating a patient in those instances such as, for example, in a pre-operative procedure, where a patient will be suffering from acute or chronic pain in the near future. In determining the therapeutically effective analgesic amount or dose, a number of factors are considered by the attending diagnostician, including, but not limited to: the species of mammal; its size, age, and general health; the specific disease involved; the degree of or involvement or the severity of the disease; the response of the individual patient; the particular compound administered; the mode of administration; the bioavailability characteristics of the preparation administered; the dose regimen selected; the use of concomitant medication; and other relevant circumstances.

A therapeutically effective analgesic amount of a compound of formulae (1), (2), (3), (4) or (5) is expected to vary from about 0.1 milligram per kilogram of body weight per day (mg/kg/day) to about 100 mg/kg/day. Preferred amounts are expected to vary from about 0.5 to about 10 mg/kg/day.

Furthermore, the compounds of the present invention are useful in their pharmacological activities such as tachykinin antagonism, especially neurokinin A antagonism. One object of the present invention is to provide new and useful antagonists of neurokinin A. Because the compounds of the present invention are tachykinin antagonists, they are useful in the treatment of conditions associated with inflammation, including asthma, allergies, bronchitis, rhinitis, Crohn's disease, ulcerative colitis, rheumatoid arthritis, osteoarthritis, migraine, cystitis and hypersensitivity reactions. Tachykinin antagonism is also appropriate therapy for the treatment of pain, peripheral neuropathy, emesis, chronic cough, post-herpetic neuralgia, adverse immunological reactions, blood flow disorders due to vasodilatation, ophthalmic diseases, such as conjunctivitis and cutaneous diseases such as contact dermatitis, atopic dermatitis, urticaria and the like. Various central nervous system disorders including anxiety, depression, psychosis, schizophrenia and dementia are also amenable to treatment with tachykinin antagonists.

The compounds of this invention are highly potent antagonists to neurokinin A and exhibit a selectivity of action towards $NK_2$ receptors vs. $NK_1$ receptors. It is believed that the compounds of this invention exert their inhibitory effect through antagonism of $NK_2$ receptors and thereby provide relief for neurokinin A-mediated diseases including but not limited to acute and chronic pain, as well as asthma and other inflammatory conditions of the lung. However, it is understood that the present invention is not limited by any particular theory or proposed mechanism to explain its effectiveness in an end-use application.

In effecting treatment of a patient afflicted with a disease state described above, a compound of formula (1), (2), (3), (4) or (5) can be administered in any form or mode which makes the compound bioavailable in effective amounts, including oral, aerosol, and parenteral routes. For example, compounds of formulae (1), (2), (3), (4) or (5) can be administered orally, by aerosolization, subcutaneously, intramuscularly, intravenously, transdermally, intranasally, rectally, topically, and the like. Oral or aerosol administration is generally preferred. One skilled in the art of preparing formulations can readily select the proper form and mode of administration depending upon the particular characteristics of the compound selected the disease state to be treated, the stage of the disease, and other relevant circumstances. Remington's Pharmaceutical Sciences, 18th Edition, Mack Publishing Co. (1990).

The compounds can be administered alone or in the form of a pharmaceutical composition in combination with pharmaceutically acceptable carriers or excipients, the proportion and nature of which are determined by the solubility and chemical properties of the compound selected, the chosen route of administration, and standard pharmaceutical practice. The compounds of the invention, while effective themselves, may be formulated and administered in the form of their pharmaceutically acceptable salts, such as for example, acid addition salts, for purposes of stability, convenience of crystallization, increased solubility and the like.

In another embodiment, the present invention provides compositions comprising a compound of formula (1), (2), (3), (4) or (5) in admixture or otherwise in association with one or more inert carriers. These compositions are useful, for example, as assay standards, as convenient means of making bulk shipments, or as pharmaceutical compositions. An assayable amount of a compound of formula (1), (2), (3), (4) or (5) is an amount which is readily measurable by standard assay procedures and techniques as are well known and appreciated by those skilled in the art. Assayable amounts of a compound of formula (1), (2), (3), (4) or (5) will generally vary from about 0.001% to about 75% of the composition by weight. Inert carriers can be any material which does not degrade or otherwise covalently react with a compound of formula (1), (2), (3), (4) or (5). Examples of suitable inert carriers are water; aqueous buffers, such as those which are generally useful in High Performance Liquid Chromatography (HPLC) analysis; organic solvents, such as acetonitrile, ethyl acetate, hexane and the like; and pharmaceutically acceptable carriers or excipients.

More particularly, the present invention provides pharmaceutical compositions comprising a therapeutically effective amount of a compound of formula (1), (2), (3), (4) or (5) in admixture or otherwise in association with one or more pharmaceutically acceptable carriers or excipients.

The pharmaceutical compositions are prepared in a manner well known in the pharmaceutical art. The carrier or excipient may be a solid, semi-solid, or liquid material which can serve as a vehicle or medium for the active ingredient. Suitable carriers or excipients are well known in the art. The pharmaceutical composition may be adapted for oral, parenteral, or topical use and may be administered to the patient in the form of tablets, capsules, suppositories, solution, suspensions, or the like.

The compounds of the present invention may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% of the compound of the invention, the active ingredient, but may be varied depending upon the particular form and may conveniently be between 4% to about 70% of the weight of the unit. The amount of the compound present in compositions is such that a suitable dosage will be obtained. Preferred compositions and preparations according to the present invention are prepared so that an oral dosage unit form contains between 5.0–300 milligrams of a compound of the invention. The tablets, pills, capsules, troches and the like may also contain one or more of the following adjuvants: binders such as microcrystalline cellulose, gum tragacanth or gelatin; excipients such as starch or lactose, disintegrating agents such as alginic acid, Primogel, corn starch and the like; lubricants such as magnesium stearate or Sterotex; glidants such as colloidal silicon dioxide; and sweetening agents such as sucrose or saccharin may be added or a flavoring agent such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the present compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the compounds of the present invention may be incorporated into a solution or suspension. These preparations should contain at least 0.1% of a compound of the invention, but may be varied to be between 0.1 and about 50% of the weight thereof. The amount of the inventive compound present in such compositions is such that a suitable dosage will be obtained. Preferred compositions and preparations according to the present invention are prepared so that a parenteral dosage unit contains between 5.0 to 100 milligrams of the compound of the invention.

The compounds of formula (1), (2), (3), (4) or (5) of the present invention may also be administered by aerosol. The term aerosol is used to denote a variety of systems ranging from those of colloidal nature to systems consisting of pressurized packages. Delivery may be by a liquified or compressed gas or by a suitable pump system which dispenses the active ingredients. Aerosols of compounds of formula 1 may be delivered in single phase, bi-phasic, or tri-phasic systems in order to deliver the active ingredient. Delivery of the aerosol includes the necessary container, activators, valves, subcontainers, and the like. Preferred aerosol are able to be determined by one skilled in the art.

The compounds of formula (1), (2), (3), (4) or (5) of this invention may also be administered topically, and when done so the carrier may suitably comprise a solution, ointment or gel base. The base, for example, may comprise one or more of the following: petrolatum, lanolin, polyethylene glycols, bee wax, mineral oil, diluents such as water and alcohol, and emulsifiers and stabilizers. Topical formulations may contain a concentration of the formula 1 or its pharmaceutical salt from about 0.1 to about 10% w/v (weight per unit volume).

The solutions or suspensions may also include one or more of the following adjuvants: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

As used herein, the term "patient" refers to a warm blooded animal such as a mammal which is afflicted with a particular inflammatory disease state. It is understood that guinea pigs, dogs, cats, rats, mice, horses, cattle, sheep, and humans are examples of animals within the scope of the meaning of the term.

EXAMPLE 29

ANTAGONISM OF IODINATED TACHYKININ BINDING TO $NK_1$ AND $NK_2$ RECEPTORS BY PUTATIVE ANTAGONISTS

Receptor binding assays were performed in crude tissue membranes. The NK-1 receptor binding affinity of proposed tachykinin antagonists was evaluated in guinea pig lungs (Keystone Biologicals, Cleveland, OH, kept frozen at −80° C. until use). Affinity for the NK-2 receptor was evaluated in HSKR-1 cells which are mouse 3T3 fibroblasts expressing the human jejunal NK-2 receptor. Tissues or cells were homogenized with a Polytron in 15 volumes of 50 mM Tris-HCl buffer (pH 7.4, 4° C.) containing 120 mM NaCl and 5 mM KCl and centrifuged at 48,000×g for 12 min. at 4° C. The pellet was resuspended in 15 volumes of 50 mM Tris-HCl buffer containing 10 mM EDTA and 300 mM KCl then set on ice for 30 min. The suspension was cetrifuged as above and the pellet washed by resuspension and cetrifugation two additional times in 50 mM Tris-HCl buffer (pH 7.4, 4° C.). The final pellet was resuspended in a concentration of 20 mg/ml in incubation buffer then kept at room temperature for at least 15 min prior to use. Receptor binding was initiated by addition of 250 µl membrane preparation (final protein concentration; lungs=286 µg/tube, HSKR-1 cells=100 µg/tube) in duplicate to 0.1 nM of the following radioligands: for NK-1 receptor assays, $^{125}$I-Bolton-Hunter Lys-3 labeled substance P (New England Nuclear, specific activity, 2200 Ci/mmol); for NK-2 receptor assays, $^{125}$iodohistidyl-1-neurokinin A (Amersham, specific activity, 2000 Ci/mmol) in a final volume of 500 µl of buffer containing 50 mM Tris-HCl (pH 7.4 at room temperature), 0.1% bovine serum albumin, 2 mM $MnCl_2$, 40 µg/ml bacitracin, 4 µg/ml leupeptin and chymostatin, 1 µM thiorphan and various doses of the tachykinin antagonists. Incubations were performed at room temperature for 90 min (NK-1 receptor assays) or 2 hr (NK-2 receptor assays); binding was terminated by addition of 50 mM Tris-HCl buffer (pH 7.4, 4° C.) and filtration under vacuum through GF/B filters presoaked with 0.1% polyethyleneimine (NK-1 receptor assays) or 0.5% bovine serum albumin (NK-2 receptor assays). Nonspecific binding was defined as binding in the presence of 1 µM substance P (NK-1 receptor assays) or neurokinin A (NK-2 receptor assays) (Peptides International, Inc., Louisville, Ky.). Specific binding was calculated by subtracting nonspecific binding from total binding and corresponded to 70–90% of total binding. Data were analyzed and $IC_{50}$ values generated by nonlinear regression using an iterative curve fitting program (Graph-PAD Inplot, San Diego, Calif.). Protein was determined by the method of Lowry.

Tachykinin receptor binding affinities of the compounds are presented in Table 2. Several of the compounds presented, including cyclo[Tyr-trp-Leu-Arg-Trp-Gly] SEQ. ID 6, exhibit high affinity and selectivity for NK-2 receptors.

TABLE 2

NK-1 & NK-2 RECEPTOR BINDING AFFINITIES

| Peptide Sequence | IC$_{50}$(nM) | |
|---|---|---|
| | NK-1 | NK-2 |
| cyclo[Tyr—Trp—Leu—Arg—Trp—Gly] | 10,000 | 305 ± 31 |
| cyclo[Tyr—trp—Ala—Arg—Trp—Gly] |  | 56.7 ± 5.45 |
| cyclo[tyr—trp—Leu—Arg—Trp—Gly] | >10,000 | 4.97 ± 0.42 |
| cyclo[tyr—trp—Leu—Arg—Tyr—Gly] | >10,000 | 18.9 ± 1.58 |
| cyclo[tyr—Gln—Leu—Arg—Trp—Gly] |  | 407 ± 52 |
| cyclo[Tyr—trp—Leu—Arg—Trp—ala] |  | 7.99 ± 1.02 |
| cyclo[Tyr—trp—Leu—Arg—trp—Gly] | >10,000 | 193 ± 11.5 |
| cyclo[Tyr—trp—Leu—Arg—Trp—Ala] |  | 9.90 ± 0.90 |
| cyclo[Tyr—trp—Leu—Arg—Trp—Pro] | 5167 ± 507 | 30 ± 2.52 |
| cyclo[Leu—Arg—Trp—Gly—Leu—Arg—Trp—Gly] |  | 768 ± 75 |
| cyclo[Trp—trp—Leu—Arg—Trp—Gly] | 4833 ± 297 | 4.7 ± 0.15 |
| cyclo[Tyr—trp—Leu—Arg—Tyr—Ala] |  | 206 ± 15 |
| cyclo[Tyr—trp—Leu—Arg—Gly—Trp] |  | 360 ± 21 |
| cyclo[Tyr—Trp—Tyr—gln—Leu—Arg—Trp—Gly] | >10,000 | 27.0 ± 0.82 |
| cyclo[Tyr—trp—Leu—Arg—Trp—Gly] | 6187 ± 277 | 6.79 ± 0.69 |
| cyclo[Tyr—trp—Leu—Arg—(p-NH$_2$—Phe)—Gly] | >10,000 | 20.2 ± 2.03 |
| cyclo[Tyr—trp—Pro—Arg—Trp—Gly] | >10,000 | 5.13 ± 0.36 |
| cyclo[Tyr—trp—Leu—Arg—(p-NO$_2$—Phe)—Gly] | >10,000 | 11.7 ± 0.44 |
| cyclo[Tyr—trp—Leu—Arg—(p-Cl—Phe)—Gly] | ~10,000 | 13.3 ± 1.31 |
| cyclo[Tyr—trp—Leu—Arg—(Flg)—Gly](II) | 2766 ± 16.5 | 993 ± 36.5 |
| cyclo[Tyr—trp—Leu—Arg—(Dpa)—Gly](II) | 4691 ± 11 | 878 ± 162 |
| cyclo[Phe—phe—Pro—Arg—Phe—Gly] | 9314 ± 2074 | 674 ± 57 |
| cyclo[Tyr—trp—Leu—Arg—(Flg)—Gly](I) | 3642 ± 425 | 123 ± 1.86 |
| cyclo[Tyr—trp—Leu—Arg—(Dpa)—Gly](I) | 12,077 ± 2044 | 2903 ± 371 |

Data are mean ± S.E.M. from 2–72 experiments

EXAMPLE 30

ANTAGONISM OF NK-2 RECEPTOR MEDIATED PHOSPHATIDYLINOSITOL TURNOVER

Cultured SKLKB82#3 (bovine stomach NK-2 receptor transfected into mouse fibroblast cell line) cells were seeded onto 24-well plates at 125,000 cells/well, two-three days prior to assay. Cells were loaded with 0.5 ml of 0.2 µM myo[2-$^3$H(N)] inositol (American Radiolabeled Chemicals Inc., specific activity, 20 Ci/mmol) 20–24 hrs prior to assay. Cultured cells were maintained at 37° C. in a 5% CO$_2$ environment. On the day of the assay, media was aspirated and the cells incubated in D-MEM/F-12 media containing 40 µg/ml bacitracin, 4 µg/ml each of leupeptin and chymostatin, 0.1% bovine serum albumin and 1 µM thiorphan and 10 mM LiCl. After 15 min., cyclo[Tyr-trp-Leu-Arg-Trp-Gly] SEQ. ID 6 (concentration range 0.3 nM –10 µM) was added to the cells in a volume of 0.1 ml. NKA or incubation buffer (for control) were added 15 min. later at various concentrations (0.1 nM–10 µM in a volume=0.1 ml) and incubated for 60 min. in a final volume of 1 ml. To terminate the reaction, media was aspirated and 0.1 ml methanol added to all wells. Two aliquots of 0.5 ml methanol were added to the wells to harvest the cells into chloroform resistant tubes. Chloroform (1 ml) was added to each tube containing the methanol/cell suspension followed by 0.5 ml ddH$_2$O. The tubes were then vortexed for 15 sec. and centrifuged for 10 min. at 1700×g. An aliquot of 0.9 ml of the aqueous phase was removed and placed in chloroform resistant tubes containing 2 ml ddH$_2$O. Samples were vortexed and loaded onto a 1 ml 50% Bio-Rad AG 1-X8 (formate form, 100–200 mesh) exchange column (Bio-Rad Laboratories, Hercules, Calif.). The columns were then washed, in order, with: 1) 10 ml ddH$_2$O, 2) 5 ml of 5 mM disodium tetraborate/60 mM sodium formate, and 3) 2 ml of 1M ammonium formate/ 0.1M formic acid. The third elution was collected and counted in 9 ml scintillation fluid. A 50 µl aliquot of the organic (bottom) phase was removed, dried in a scintillation vial and counted in 7 ml scintillation fluid.

The ratio of DPM in the aqueous phase aliquot (total inositol phosphates) to the DPM in the 50 µl organic phase aliquot (total [$^3$H]-inositol incorporated) was calculated for each sample. Data are expressed as a percent of agonist-induced accumulation of [3H]-inositol phosphates over basal leTels. Antagonist activity was apparent by the rightward shift of the dose-response curves to the tachykinins in the presence of cyclo[Tyr-trp-Leu-Arg-Trp-Gly] SEQ. ID 6. Schild regression analysis using three or more antagonist concentrations were used to derive pA$_2$ and slope values.

Dose-response curves were constructed and the ability of the test compound to inhibit tachykinin-induced phosphatidylinositol (PI) turnover was determined using the method of Bristow et al., *Br. J. Pharmacol.*, 90: 211–21 (1987) with the aid of the computer program, GraphPad Inplot. FIG. 1 illustrates the ability of cyclo[Tyr-trp-Leu-Arg-Trp-Gly] SEQ. ID 6 to produce dose-related antagonism of NKA-induced PI turnover in SKLKB82#3 cells. Data are expressed as percent stimulation of total inositol phosphate accumulation over basal levels and normalized to the maximum response produced by NKA. These data demonstrate that cyclo[Tyr-trp-Leu-Arg-Trp-Gly] SEQ. ID 6 has no agonist activity (as indicated by its failure to stimulate PI turnover, even at high doses of the compound) and antagonizes the action of NKA at NK-2 (on SKLKB82#3) receptors (pA$_2$=8.45(95% confidence limits=8.22 to 8.69) and slope=–0.85(95% confidence limits=–0.94 to –0.75).

EXAMPLE 31

ANTAGONISM OF NKA AND CAPSAICIN INDUCED RESPIRATORY EFFECTS IN CONSCIOUS GUINEA PIGS

In vivo experiments were performed using male Duncan Hartley guinea pigs (250–350 grams). Changes in conscious breathing patterns were monitored in four animals simultaneously, using modified whole body plethysmography consisting of four small plexiglass boxes each connected to its own reference box via Validyne DP 45-16 differential pressure transducers. The 4 boxes were equipped with an air supply line (also used for aerosol delivery) and an exhaust air line. Supply and exhaust lines were of the same length and narrow bore and arose from a common supply chamber and vented to a common exhaust chamber. This system was used to ensure that fluctuations in air supply and atmospheric pressure would remain in phase and be eliminated from the net signal by the differential pressure transducers. The analog pressure signals were digitalized via a Data Translation DT2821 A to D board. Data were collected at a rate of 100 samples/second/animal. Each cycle of pressure change was analyzed using the following parameters: rising and falling slope determined between minimum and maximum pressures, the ratio of rising over falling slope, and the magnitude of the change between initial trough pressure and peak cycle pressure. Using these values (and observing the animals) the pressure cycles were characterized into normal breaths, forced exhalations (apparent abdominal heaving), significant respiratory events (SREs; usually coughs, less often sneezes or gasps which were characterized by transient, extremely large pressure increases which were distinguishable from noise) and movement/noise with a PCAT 286 running a System V UNIX operating system. Dyspnea was defined as a significant, sustained increase in plethysmograpy pressure which was associated with an observable shift to labored breathing in the animal.

During the course of a typical experiment in which airway responsiveness to various bronchoconstricting agents was examined, aerosols were delivered for 19 min (0.33 ml/min) using a DeVilbiss Ultraneb 99 ultrasonic nebulizer and animals monitored during this time. Prior to nebulization, 1 min of resting breathing was collected to establish a baseline pressure. In preliminary experiments, various concentrations of the bronchoconstrictive agents were evaluated and a concentration chosen which maximized the number of animals exhibiting dyspnea but minimized the severity of the response. Hence, neurokinin A was delivered at a final concentration of 0.05%, and capsaicin, 0.001%. The vehicle for nebulization of all bronchoconstrictive agents was phosphate buffered saline (pH 7.4) which elicited no respiratory effects itself. Cyclo[Tyr-trp-Leu-Arg-Trp-Gly] SEQ. ID 6 was administered (i.v.) 20 mir prior to onset of aerosol exposure.

Table 3 illustrates the effects of cyclo[Tyr-trp-Leu-Arg-Trp-Gly] SEQ. ID 6 on various respiratory effects induced by NFA or capsaicin aerosols. At a dose of 5 mg/kg i.v., the compound completely inhibited the respiratory effects induced by NKA aerosol in consious guinea pigs. Lower doses (0.5–2.5 mg/kg, i.v.) of the cyclic peptide delayed the onset of dyspnea and SREs produced by the tachykinin. These data suggest that cyclo[Tyr-trp-Leu-Arg-Trp-Gly] SEQ. ID 6 is an NK-2 receptor antagonist in guinea pig airways in vivo.

The cyclic peptide, cyclo[Tyr-trp-Leu-Arg-Trp-Gly] SEQ. ID 6, also inhibited the respiratory effects produced in response to endogenous tachykinins which were released by capsaicin aerosol (Table 3). Although cyclo[Tyr-trp-Leu-Arg-Trp-Gly] SEQ. ID 6 only reduced the incidence of capsicin-induced dyspnea by 20%, the onset of dyspnea was delayed almost 2-fold; the number of SREs produced in response to capsaicin was also reduced and their onset increased, suggesting antitussive properties of the compound.

TABLE 3

EFFECTS OF Cyclo[Tyr—trp—Leu—Arg—Trp—Gly] ON RESPIRATORY EFFECTS INDUCED BY NKA OR CAPSAICIN AEROSOLS IN CONSCIOUS GUINEA PIGS A. NKA Aerosol

| Pre-treatment | Dyspnea Incidence | Dyspnea Onset (sec) | SRE No. | SRE Onset (sec) |
|---|---|---|---|---|
| Control Peptide | 100% | 403 ± 37 | 8.17 ± 1.92 | 435 ± 28 |
| 5 mg/kg,iv | 0%* | — | 0* | |
| 2.5 mg/kg,iv | 100% | 725 ± 80* | 8.00 ± 0.82 | 791 ± 70* |
| 1 mg/kg,iv | 100% | 729 ± 66* | 6.33 ± 0.88 | 816 ± 65* |
| 0.5 mg/kg,iv | 100% | 521 ± 29 | 7.75 ± 2.21 | 602.5 ± 32 |

Data are mean ± S.E.M. of values from 4–18 animals per treatment. SRE = significant respiratory event, usually coughs and less often, gasps. Asterisks indicate significant difference from control ($p < 0.05$). Peptide = Cyclo[Tyr—trp—Leu—Arg—Trp—Gly].

B. Capsaicin Aerosol

| | | | | |
|---|---|---|---|---|
| Control Peptide | 100% | 204 ± 30 | 14.9 ± 2.88 | 288 ± 39 |
| 5 mg/kg,iv | 80% | 470 ± 78* | 8.11 ± 1.22* | 352 ± 92 |

Data are mean ± S.E.M. of values 10 animals per treatment. SRE = significant respiratory event, usually coughs and less often, gasps. Asterisks indicate significant difference from control ($p < 0.05$). Peptide = Cyclo[Tyr—trp—Leu—Arg—Trp—Gly].

EXAMPLE 32

INHIBITION OF ACETIC ACID-INDUCED WRITHING IN MICE

The analgesic potential of the compounds of this invention was measured using a modification of the method of Whittle (Br. J. Pharmacol. 22:2246, 1964). Groups of 5–10 male mice received an intrathecal injection of cyclo[Tyr-trp-Leu-Arg-Trp-Gly] SEQ. ID 6 (0.013-4µg) or ethanol/saline vehicle in a volume of 5 µl. After 5 minutes, mice received an intraperitoneal injection of 0.4 ml acetic acid (0.25% v/v). Five minutes later, the mice were observed for 15 minutes for the appearance of squirming (abdominal writhing) and the number of squirms for each mouse was counted. To calculate an $ED_{50}$ (dose producing analgesia in 50% of the mice), four or more doses of compound were tested and the results subjected to quantal analysis with an appropriate computer program.

The cyclic peptide, cyclo[Tyr-trp-Leu-Arg-Trp-Gly] SEQ. ID 6 inhibited acetic acid-induced writhing in mice with an $ED_{50}$=0.18 µg (95% confidence limits=0.03–0.58).

What is claimed is:

1. A tachykinin NK-2 receptor antagonizing peptide having the formulae
cyclo[Trp-trp-Leu-Arg-Trp-Gly], SEQ. ID 7
cyclo[tyr-Gln-Leu-Arg-Trp-Gly], SEQ. ID 15
cyclo[Tyr-trp-Pro-Arg-Trp-Gly], or SEQ. ID 18
cyclo[Phe-phe-Pro-Arg-Phe-Gly]; SEQ. ID 19
or a pharmaceutically acceptable salt thereof.

2. A tachykinin NK-2 receptor antagonizing peptide of claim 1 having the formula cyclo[Trp-trp-Leu-Arg-Trp-Gly], SEQ. ID 7.

3. A tachykinin NK-2 receptor antagonizing peptide of claim 1 having the formula cyclo[tyr-Gln-Leu-Arg-Trp-Gly], SEQ. ID 15.

4. A tachykinin NK-2 receptor antagonizing peptide of claim 1 having the formulae cyclo[Tyr-trp-Pro-Arg-Trp-Gly] SEQ. ID 18 or cyclo[Phe-phe-Pro-Arg-Phe-Gly], SEQ. ID 19.

5. A compound which is a tachykinin NK-2 receptor antagonizing peptide selected from:
cyclo[Leu-Arg-Trp-Gly-Leu-Arg-Trp-Gly] or SEQ. ID 20
cyclo[Tyr-Trp-Tyr-gly-Leu-Arg-Trp-Gly]; SEQ. ID 21
or a pharmaceutically acceptable salt thereof.

6. A compound of claim 5 wherein said compound is cyclo[Tyr-Trp-Tyr-gln-Leu-Arg-Trp-Gly], SEQ. ID 21.

7. A compound which is tachykinn NK-2 receptor antagonizing peptide selected from:
cyclo[Tyr-trp-Leu-Arg-Nal-Gly], SEQ. ID 22
cyclo[Tyr-trp-Leu-Arg-(p-$NO_2$-Phe)-Gly], SEQ. ID 23
cyclo[Tyr-trp-Leu-Arg-(p-$NH_2$-Phe)-Gly], SEQ. ID 24
cyclo[Tyr-trp-Leu-Arg-(p-Cl-Phe)-Gly], SEQ. ID 25
cyclo[Tyr-trp-Leu-Arg-(Tiq-OH)-Gly], SEQ. ID 36
cyclo[Tyr-trp-Leu-Arg-(tiq)-Gly], SEQ. ID 35
cyclo[Tyr-trp-Leu-Arg-(Tiq)-Gly], SEQ. ID 34
cyclo[Tyr-trp-Leu-Arg-(Me-Tyr)-Gly], SEQ. ID 33
cyclo[Tyr-trp-Leu-Arg-(Flg)-Gly](II) or SEQ. ID 30
cyclo[Tyr-trp-Leu-Arg-(Flg)-Gly](I); SEQ. ID 29
or a pharmaceutically acceptable salt thereof.

8. A compound of claim 7 wherein said compound is cyclo[Tyr-trp-Leu-Arg-(p-$NO_2$-Phe)-Gly], SEQ. ID 23.

9. A compound of claim 7 wherein said compound is cyclo[Tyr-trp-Leu-Arg-(p-$NH_2$-Phe)-Gly], SEQ. ID 24.

10. A compound of claim 7 wherein said compound is cyclo[Tyr-trp-Leu-Arg-(p-Cl-Phe)-Gly], SEQ. ID 25.

11. A pharmaceutical composition comprising a peptide of claim 1 and a pharmaceutically acceptable carrier.

12. A pharmaceutical composition comprising a peptide of claim 5 and a pharmaceutically acceptable carrier.

13. A pharmaceutical composition comprising a peptide of claim 7 and a pharmaceutically acceptable carrier.

14. A method for the treatment of a patient afflicted with a respiratory disease comprising the administration to said patient a therapeutically effective amount of a compound selected from the group consisting of
cyclo[Tyr-trp-Leu-Arg-Trp-Gly], SEQ. ID 6
cyclo[Trp-trp-Leu-Arg-Trp-Gly], SEQ. ID 7
cyclo[tyr-trp-Leu-Arg-Trp-Gly], SEQ. ID 8
cyolo[Tyr-trp-Leu-Arg-Tyr-Gly], SEQ. ID 9
cyclo[Tyr-trp-Leu-Arg-Trp-Ala], SEQ. ID 10
cyclo[Tyr-trp-Leu-Arg-Trp-ala], SEQ. ID 11
cyclo[Tyr-Trp-Leu-Arg-Trp-Gly], SEQ. ID 12
cyclo[Tyr-trp-Ala-Arg-Trp-Gly], SEQ. ID 13
cyclo[Tyr-trp-Leu-Arg-trp-Gly], SEQ. ID 14
cyclo[tyr-Gln-Leu-Arg-Trp-Gly], SEQ. ID 15
cyclo[Tyr-trp-Leu-Arg-Tyr-Ala], SEQ. ID 16
cyclo[Tyr-trp-Leu-Arg-Gly-Trp], SEQ. ID 17
cyclo[Tyr-trp-Pro-Arg-Trp-Gly], and SEQ. ID 18
cyclo[Phe-phe-Pro-Arg-Phe-Gly]; SEQ. ID 19
or a pharmaceutically acceptable salt thereof.

15. A method according to claim 14 wherein said compound is selected from the group consisting of
cyclo[Tyr-trp-Leu-Arg-Trp-Gly], SEQ. ID 6
cyclo[Trp-trp-Leu-Arg-Trp-Gly], and SEQ. ID 7
cyclo[tyr-trp-Leu-Arg-Trp-Gly], SEQ. ID 8.

16. A method according to claim 14 wherein said compound is cyclo[Tyr-trp-Leu-Arg-Trp-Gly], SEQ. ID 6.

17. A method according to claim 14 wherein said compound is selected from the group consisting of
cyclo[Tyr-trp-Leu-Arg-Tyr-Gly], SEQ. ID 9
cyclo[Tyr-trp-Leu-Arg-Trp-Ala], and SEQ. ID 10
cyclo[Tyr-trp-Leu-Arg-Trp-ala], SEQ. ID 11.

18. A method according to claim 14 wherein said respiratory disease is asthma.

19. A method for the treatment of a patient afflicted with a respiratory disease comprising the administration thereto of a therapeutically effective amount of a compound of claim 5.

20. A method according to claim 19 wherein said respiratory disease is asthma.

21. A method for the treatment of a patient afflicted with a respiratory disease comprising the administration thereto of a therapeutically effective amount of a compound of claim 7.

22. A method according to claim 21 wherein said respiratory disease is asthma.

23. A method for providing an analgesic effect in a patient in need thereof, comprising the administration to said patient a therapeutically effective amount of a compound selected from the group consisting of
cyclo[Tyr-trp-Leu-Arg-Trp-Gly], SEQ. ID 6
cyclo[Trp-trp-Leu-Arg-Trp-Gly], SEQ. ID 7
cyclo[tyr-trp-Leu-Arg-Trp-Gly], SEQ. ID 8
cyclo[Tyr-trp-Leu-Arg-Tyr-Gly], SEQ. ID 9
cyclo[Tyr-trp-Leu-Arg-Trp-Ala], SEQ. ID 10
cyclo[Tyr-trp-Leu-Arg-Trp-ala], SEQ. ID 11
cyclo[Tyr-Trp-Leu-Arg-Trp-Gly], SEQ. ID 12
cyclo[Tyr-trp-Ala-Arg-Trp-Gly], SEQ. ID 13
cyclo[Tyr-trp-Leu-Arg-trp-Gly], SEQ. ID 14
cyclo[tyr-Gln-Leu-Arg-Trp-Gly], SEQ. ID 15
cyclo[Tyr-trp-Leu-Arg-Tyr-Ala], SEQ. ID 16 cyclo[Tyr-trp-Leu-Arg-Gly-Trp], SEQ. ID 17
cyclo[Tyr-trp-Pro-Arg-Trp-Gly], and SEQ, ID 18
cyclo[Phe-phe-Pro-Arg-Phe-Gly]; SEQ. ID 19
or a pharmaceutically acceptable salt thereof.

24. A method according to claim 23 wherein said compound is selected from the group consisting of
cyclo[Tyr-trp-Leu-Arg-Trp-Gly], SEQ. ID 6
cyclo[Trp-trp-Leu-Arg-Trp-Gly], and SEQ. ID 7
cyclo[tyr-trp-Leu-Arg-Trp-Gly], SEQ. ID 8.

25. A method according to claim 23 wherein said compound is cyclo[Tyr-trp-Leu-Arg-Trp-Gly], SEQ. ID 6.

26. A method for providing an analgesic effect in a patient in need thereof, comprising the administration thereto of a therapeutically effective analgesic amount of a compound of claim 5.

27. A method for providing an analgesic effect in a patient in need thereof, comprising the administration thereto of a therapeutically effective analgesic amount of a compound of claim 7.

* * * * *

UNITED STATES PATENT AND TRADEMARK OFFICE
CERTIFICATE OF CORRECTION

PATENT NO. : 5,521,156
DATED : May 28, 1996
INVENTOR(S) : Thomas J. Owen, et al

It is certified that error appears in the above-identified patent and that said Letters Patent is hereby corrected as shown below:

At column 3, line 31, the patent reads "$(CH_2)_3$ 13 NHC" and should read -- $(CH_2)_3$-NHC --.
At column 6, line 39, the patent reads "orthiophospate" and should read --orthophosphate--.
At column 10, line 5, the patent reads "i s" (twice) and should read --is--.
At column 10, line 65, the patent reads "group group" and should read --group--.
At column 14, line 64, the patent reads "1,07" and should read --1.07--.
At column 18, line 9, the patent reads "-$C_1$" and should read --Cl--.
At column 20, line 2, the patent reads "of the compound selected the" and should read --of the compound selected, the--.
At column 21, line 44, the patent reads "aerosol" and should read --aerosols--.
At column 22, line 26, the patent reads "48,000xg" and should read --48,000 xg--.
At column 24, line 38, the patent reads "basal leTels" and should read --basal levels--.
At column 25, line 28, the patent reads "plethysmograpy" and should read --plethysmograph--.
At column 25, line 46, the patent reads "mir" and should read --min--.
At column 47, line 33, claim 5, should read --Tyr- Glu-Leu--.
At column 47, line 36, claim 6, change "gln" to --glu--.
At column 48, line 13, claim 14, should read "cyolo" and should read --cyclo--.

Signed and Sealed this

Tenth Day of November 1998

Attest:

BRUCE LEHMAN

*Attesting Officer*    Commissioner of Patents and Trademarks

SEQUENCE LISTING ( 1 ) GENERAL INFORMATION:

( i i i ) NUMBER OF SEQUENCES: 36

( 2 ) INFORMATION FOR SEQ ID NO:1:

( i ) SEQUENCE CHARACTERISTICS:
        ( A ) LENGTH: 6 amino acids
        ( B ) TYPE: amino acid
        ( D ) TOPOLOGY: circular ( i i ) MOLECULE TYPE: peptide ( x i ) SEQUENCE DESCRIPTION: SEQ ID NO:1:

Xaa Xaa Xaa Xaa Xaa Xaa
    1                   5

( 2 ) INFORMATION FOR SEQ ID NO:2:

( i ) SEQUENCE CHARACTERISTICS:
        ( A ) LENGTH: 6 amino acids
        ( B ) TYPE: amino acid
        ( D ) TOPOLOGY: circular ( i i ) MOLECULE TYPE: peptide ( i x ) FEATURE:
        ( A ) NAME/KEY: Modified-site
        ( B ) LOCATION: 2
        ( D ) OTHER INFORMATION: /note="Xaa at location 2 is
            tryptophan in the D-configuration"

( x i ) SEQUENCE DESCRIPTION: SEQ ID NO:2:

Xaa Xaa Leu Arg Trp Xaa
    1                   5

( 2 ) INFORMATION FOR SEQ ID NO:3:

( i ) SEQUENCE CHARACTERISTICS:
        ( A ) LENGTH: 8 amino acids
        ( B ) TYPE: amino acid
        ( D ) TOPOLOGY: circular ( i i ) MOLECULE TYPE: peptide ( x i ) SEQUENCE DESCRIPTION: SEQ ID NO:3:

Xaa Xaa Xaa Xaa Leu Arg Trp Gly
    1                   5

( 2 ) INFORMATION FOR SEQ ID NO:4:

( i ) SEQUENCE CHARACTERISTICS:
        ( A ) LENGTH: 6 amino acids
        ( B ) TYPE: amino acid
        ( D ) TOPOLOGY: circular ( i i ) MOLECULE TYPE: peptide ( i x ) FEATURE:
        ( A ) NAME/KEY: Modified-site
        ( B ) LOCATION: 2
        ( D ) OTHER INFORMATION: /note="Xaa at location 2 is
            tryptophan in the D-configuration"

( x i ) SEQUENCE DESCRIPTION: SEQ ID NO:4:

Xaa Xaa Leu Arg Xaa Xaa
    1                   5

( 2 ) INFORMATION FOR SEQ ID NO:5:

( i ) SEQUENCE CHARACTERISTICS:
        ( A ) LENGTH: 6 amino acids (B) TYPE: amino acid
(D) TOPOLOGY: circular (ii) MOLECULE TYPE: peptide (xi) SEQUENCE DESCRIPTION: SEQ ID NO:5:

Xaa Xaa Xaa Arg Xaa Xaa
1               5

(2) INFORMATION FOR SEQ ID NO:6:

(i) SEQUENCE CHARACTERISTICS:
      (A) LENGTH: 6 amino acids
      (B) TYPE: amino acid
      (D) TOPOLOGY: circular (ii) MOLECULE TYPE: peptide (ix) FEATURE:
      (A) NAME/KEY: Modified-site
      (B) LOCATION: 2
      (D) OTHER INFORMATION: /note="Xaa at location 2 is
          tryptophan in the D-configuration"

(xi) SEQUENCE DESCRIPTION: SEQ ID NO:6:

Tyr Xaa Leu Arg Trp Gly
1               5

(2) INFORMATION FOR SEQ ID NO:7:

(i) SEQUENCE CHARACTERISTICS:
      (A) LENGTH: 6 amino acids
      (B) TYPE: amino acid
      (D) TOPOLOGY: circular (ii) MOLECULE TYPE: peptide (ix) FEATURE:
      (A) NAME/KEY: Modified-site
      (B) LOCATION: 2
      (D) OTHER INFORMATION: /note="Xaa at location 2 is
          tryptophan in the D-configuration"

(xi) SEQUENCE DESCRIPTION: SEQ ID NO:7:

Trp Xaa Leu Arg Trp Gly
1               5

(2) INFORMATION FOR SEQ ID NO:8:

(i) SEQUENCE CHARACTERISTICS:
      (A) LENGTH: 6 amino acids
      (B) TYPE: amino acid
      (D) TOPOLOGY: circular (ii) MOLECULE TYPE: peptide (ix) FEATURE:
      (A) NAME/KEY: Modified-site
      (B) LOCATION: 1
      (D) OTHER INFORMATION: /note="Xaa at location 1 is
          tryosine in the D-configuration"

(ix) FEATURE:
      (A) NAME/KEY: Modified-site
      (B) LOCATION: 2
      (D) OTHER INFORMATION: /note="Xaa at location 2 is
          tryptophan in the D-configuration"

(xi) SEQUENCE DESCRIPTION: SEQ ID NO:8:

Xaa Xaa Leu Arg Trp Gly
1               5

( 2 ) INFORMATION FOR SEQ ID NO:9:

( i ) SEQUENCE CHARACTERISTICS:
        ( A ) LENGTH: 6 amino acids
        ( B ) TYPE: amino acid
        ( D ) TOPOLOGY: circular ( i i ) MOLECULE TYPE: peptide ( i x ) FEATURE:
        ( A ) NAME/KEY: Modified-site
        ( B ) LOCATION: 2
        ( D ) OTHER INFORMATION: /note="Xaa at location 2 is tryptophan in the D-configuration"

( x i ) SEQUENCE DESCRIPTION: SEQ ID NO:9:

Tyr  Xaa  Leu  Arg  Tyr  Gly
    1                        5

( 2 ) INFORMATION FOR SEQ ID NO:10:

( i ) SEQUENCE CHARACTERISTICS:
        ( A ) LENGTH: 6 amino acids
        ( B ) TYPE: amino acid
        ( D ) TOPOLOGY: circular ( i i ) MOLECULE TYPE: peptide ( i x ) FEATURE:
        ( A ) NAME/KEY: Modified-site
        ( B ) LOCATION: 2
        ( D ) OTHER INFORMATION: /note="Xaa at location 2 is tryptophan in the D-configuration"

( x i ) SEQUENCE DESCRIPTION: SEQ ID NO:10:

Tyr  Xaa  Leu  Arg  Trp  Ala
    1                        5

( 2 ) INFORMATION FOR SEQ ID NO:11:

( i ) SEQUENCE CHARACTERISTICS:
        ( A ) LENGTH: 6 amino acids
        ( B ) TYPE: amino acid
        ( D ) TOPOLOGY: circular ( i i ) MOLECULE TYPE: peptide ( i x ) FEATURE:
        ( A ) NAME/KEY: Modified-site
        ( B ) LOCATION: 2
        ( D ) OTHER INFORMATION: /note="Xaa at location 6 is alanine in the D-configuration"

( i x ) FEATURE:
        ( A ) NAME/KEY: Modified-site
        ( B ) LOCATION: 6
        ( D ) OTHER INFORMATION: /note="Xaa at location 2 is tryptophan in the D-configuration"

( x i ) SEQUENCE DESCRIPTION: SEQ ID NO:11:

Tyr  Xaa  Leu  Arg  Trp  Xaa
    1                        5

( 2 ) INFORMATION FOR SEQ ID NO:12:

( i ) SEQUENCE CHARACTERISTICS:
        ( A ) LENGTH: 6 amino acids
        ( B ) TYPE: amino acid
        ( D ) TOPOLOGY: circular ( i i ) MOLECULE TYPE: peptide ( x i ) SEQUENCE DESCRIPTION: SEQ ID NO:12:

```
Tyr  Trp  Leu  Arg  Trp  Gly
1               5
```

( 2 ) INFORMATION FOR SEQ ID NO:13:

( i ) SEQUENCE CHARACTERISTICS:
        ( A ) LENGTH: 6 amino acids
        ( B ) TYPE: amino acid
        ( D ) TOPOLOGY: circular ( i i ) MOLECULE TYPE: peptide ( i x ) FEATURE:
        ( A ) NAME/KEY: Modified-site
        ( B ) LOCATION: 2
        ( D ) OTHER INFORMATION: /note="Xaa at location 2 is
            tryptophan in the D-configuration"

( x i ) SEQUENCE DESCRIPTION: SEQ ID NO:13:

```
Tyr  Xaa  Ala  Arg  Trp  Gly
1               5
```

( 2 ) INFORMATION FOR SEQ ID NO:14:

( i ) SEQUENCE CHARACTERISTICS:
        ( A ) LENGTH: 6 amino acids
        ( B ) TYPE: amino acid
        ( D ) TOPOLOGY: circular ( i i ) MOLECULE TYPE: peptide ( i x ) FEATURE:
        ( A ) NAME/KEY: Modified-site
        ( B ) LOCATION: 2
        ( D ) OTHER INFORMATION: /note="Xaa at location 2 is
            tryptophan in the D-configuration"

( i x ) FEATURE:
        ( A ) NAME/KEY: Modified-site
        ( B ) LOCATION: 5
        ( D ) OTHER INFORMATION: /note="Xaa at location 5 is
            tryptophan in the D-configuration"

( x i ) SEQUENCE DESCRIPTION: SEQ ID NO:14:

```
Tyr  Xaa  Leu  Arg  Xaa  Gly
1               5
```

( 2 ) INFORMATION FOR SEQ ID NO:15:

( i ) SEQUENCE CHARACTERISTICS:
        ( A ) LENGTH: 6 amino acids
        ( B ) TYPE: amino acid
        ( D ) TOPOLOGY: circular ( i i ) MOLECULE TYPE: peptide ( i x ) FEATURE:
        ( A ) NAME/KEY: Modified-site
        ( B ) LOCATION: 1
        ( D ) OTHER INFORMATION: /note="Xaa at location 1 is
            tyrosine in the D-configuration"

( x i ) SEQUENCE DESCRIPTION: SEQ ID NO:15:

```
Xaa  Gln  Leu  Arg  Trp  Gly
1               5
```

( 2 ) INFORMATION FOR SEQ ID NO:16:

( i ) SEQUENCE CHARACTERISTICS:
        ( A ) LENGTH: 6 amino acids
        ( B ) TYPE: amino acid
        ( D ) TOPOLOGY: circular ( i i ) MOLECULE TYPE: peptide ( i x ) FEATURE:
    ( A ) NAME/KEY: Modified-site
    ( B ) LOCATION: 2
    ( D ) OTHER INFORMATION: /note="Xaa at location 2 is
        tryptophan in the D-configuration"

( x i ) SEQUENCE DESCRIPTION: SEQ ID NO:16:

Tyr Xaa Leu Arg Tyr Ala
1               5

( 2 ) INFORMATION FOR SEQ ID NO:17:

( i ) SEQUENCE CHARACTERISTICS:
        ( A ) LENGTH: 6 amino acids
        ( B ) TYPE: amino acid
        ( D ) TOPOLOGY: circular ( i i ) MOLECULE TYPE: peptide ( i x ) FEATURE:
        ( A ) NAME/KEY: Modified-site
        ( B ) LOCATION: 2
        ( D ) OTHER INFORMATION: /note="Xaa at location 2 is
            tryptophan in the D-configuration"

( x i ) SEQUENCE DESCRIPTION: SEQ ID NO:17:

Tyr Xaa Leu Arg Gly Trp
1               5

( 2 ) INFORMATION FOR SEQ ID NO:18:

( i ) SEQUENCE CHARACTERISTICS:
        ( A ) LENGTH: 6 amino acids
        ( B ) TYPE: amino acid
        ( D ) TOPOLOGY: circular ( i i ) MOLECULE TYPE: peptide ( i x ) FEATURE:
        ( A ) NAME/KEY: Modified-site
        ( B ) LOCATION: 2
        ( D ) OTHER INFORMATION: /note="Xaa at location 2 is
            tryptophan in the D-configuration"

( x i ) SEQUENCE DESCRIPTION: SEQ ID NO:18:

Tyr Xaa Pro Arg Trp Gly
1               5

( 2 ) INFORMATION FOR SEQ ID NO:19:

( i ) SEQUENCE CHARACTERISTICS:
        ( A ) LENGTH: 6 amino acids
        ( B ) TYPE: amino acid
        ( D ) TOPOLOGY: circular ( i i ) MOLECULE TYPE: peptide ( i x ) FEATURE:
        ( A ) NAME/KEY: Modified-site
        ( B ) LOCATION: 2
        ( D ) OTHER INFORMATION: /note="Xaa at location 2 is
            phenylalanine in the D-configuration"

( x i ) SEQUENCE DESCRIPTION: SEQ ID NO:19:

Phe Xaa Pro Arg Phe Gly
1               5

( 2 ) INFORMATION FOR SEQ ID NO:20:

( i ) SEQUENCE CHARACTERISTICS:

(A) LENGTH: 8 amino acids
                (B) TYPE: amino acid
                (D) TOPOLOGY: circular (ii) MOLECULE TYPE: peptide (xi) SEQUENCE DESCRIPTION: SEQ ID NO:20:

Leu Arg Trp Gly Leu Arg Trp Gly
        1               5

(2) INFORMATION FOR SEQ ID NO:21:

(i) SEQUENCE CHARACTERISTICS:
                (A) LENGTH: 8 amino acids
                (B) TYPE: amino acid
                (D) TOPOLOGY: circular (ii) MOLECULE TYPE: peptide (ix) FEATURE:
                (A) NAME/KEY: Modified-site
                (B) LOCATION: 4
                (D) OTHER INFORMATION: /note="Xaa at location 4 is
                        glutamic acid in the D-configuration"

(xi) SEQUENCE DESCRIPTION: SEQ ID NO:21:

Tyr Trp Tyr Xaa Leu Arg Trp Gly
        1               5

(2) INFORMATION FOR SEQ ID NO:22:

(i) SEQUENCE CHARACTERISTICS:
                (A) LENGTH: 6 amino acids
                (B) TYPE: amino acid
                (D) TOPOLOGY: circular (ii) MOLECULE TYPE: peptide (ix) FEATURE:
                (A) NAME/KEY: Modified-site
                (B) LOCATION: 2
                (D) OTHER INFORMATION: /note="Xaa at location 2 is
                        tryptophan in the D-configuration"

(ix) FEATURE:
                (A) NAME/KEY: Modified-site
                (B) LOCATION: 5
                (D) OTHER INFORMATION: /note="Xaa at location 5 is
                        napthylalanine"

(xi) SEQUENCE DESCRIPTION: SEQ ID NO:22:

Tyr Xaa Leu Arg Xaa Gly
        1               5

(2) INFORMATION FOR SEQ ID NO:23:

(i) SEQUENCE CHARACTERISTICS:
                (A) LENGTH: 6 amino acids
                (B) TYPE: amino acid
                (D) TOPOLOGY: circular (ii) MOLECULE TYPE: peptide (ix) FEATURE:
                (A) NAME/KEY: Modified-site
                (B) LOCATION: 2
                (D) OTHER INFORMATION: /note="Xaa at location 2 is
                        tryptophan in the D-configuration"

(ix) FEATURE:
                (A) NAME/KEY: Modified-site
                (B) LOCATION: 5
                (D) OTHER INFORMATION: /note="Xaa at location 5 is
                        p- nitrophenylalanine"

( x i ) SEQUENCE DESCRIPTION: SEQ ID NO:23:

Tyr Xaa Leu Arg Xaa Gly
1               5

( 2 ) INFORMATION FOR SEQ ID NO:24:

( i ) SEQUENCE CHARACTERISTICS:
        ( A ) LENGTH: 6 amino acids
        ( B ) TYPE: amino acid
        ( D ) TOPOLOGY: circular ( i i ) MOLECULE TYPE: peptide ( i x ) FEATURE:
        ( A ) NAME/KEY: Modified-site
        ( B ) LOCATION: 2
        ( D ) OTHER INFORMATION: /note="Xaa at location 2 is
            tryptophan in the D-configuration"

( i x ) FEATURE:
        ( A ) NAME/KEY: Modified-site
        ( B ) LOCATION: 5
        ( D ) OTHER INFORMATION: /note="Xaa at location 5 is
            p-NH2- phenylalanine"

( x i ) SEQUENCE DESCRIPTION: SEQ ID NO:24:

Tyr Xaa Leu Arg Xaa Gly
1               5

( 2 ) INFORMATION FOR SEQ ID NO:25:

( i ) SEQUENCE CHARACTERISTICS:
        ( A ) LENGTH: 6 amino acids
        ( B ) TYPE: amino acid
        ( D ) TOPOLOGY: circular ( i i ) MOLECULE TYPE: peptide ( i x ) FEATURE:
        ( A ) NAME/KEY: Modified-site
        ( B ) LOCATION: 2
        ( D ) OTHER INFORMATION: /note="Xaa at location 2 is
            tryptophan in the D-configuration"

( i x ) FEATURE:
        ( A ) NAME/KEY: Modified-site
        ( B ) LOCATION: 5
        ( D ) OTHER INFORMATION: /note="Xaa at location 5 is
            p- chlorophenylalanine"

( x i ) SEQUENCE DESCRIPTION: SEQ ID NO:25:

Tyr Xaa Leu Arg Xaa Gly
1               5

( 2 ) INFORMATION FOR SEQ ID NO:26:

( i ) SEQUENCE CHARACTERISTICS:
        ( A ) LENGTH: 6 amino acids
        ( B ) TYPE: amino acid
        ( D ) TOPOLOGY: circular ( i i ) MOLECULE TYPE: peptide ( i x ) FEATURE:
        ( A ) NAME/KEY: Modified-site
        ( B ) LOCATION: 2
        ( D ) OTHER INFORMATION: /note="Xaa at location 2 is
            tryptophan in the D-configuration"

( x i ) SEQUENCE DESCRIPTION: SEQ ID NO:26:

Tyr Xaa Leu Arg Trp Pro
1               5

( 2 ) INFORMATION FOR SEQ ID NO:27:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:27:

Xaa  Xaa  Xaa  Xaa  Xaa  Xaa
  1                        5

( 2 ) INFORMATION FOR SEQ ID NO:28:

( i ) SEQUENCE CHARACTERISTICS:
        ( A ) LENGTH: 6 amino acids
        ( B ) TYPE: amino acid
        ( D ) TOPOLOGY: circular ( i i ) MOLECULE TYPE: peptide ( x i ) SEQUENCE DESCRIPTION: SEQ ID NO:28:

Xaa  Xaa  Xaa  Xaa  Xaa  Xaa
  1                        5

( 2 ) INFORMATION FOR SEQ ID NO:29:

( i ) SEQUENCE CHARACTERISTICS:
        ( A ) LENGTH: 6 amino acids
        ( B ) TYPE: amino acid
        ( D ) TOPOLOGY: circular ( i i ) MOLECULE TYPE: peptide ( i x ) FEATURE:
        ( A ) NAME/KEY: Modified-site
        ( B ) LOCATION: 2
        ( D ) OTHER INFORMATION: /note="Xaa at location 2 is
            tryptophan in the D-configuration"

( i x ) FEATURE:
        ( A ) NAME/KEY: Modified-site
        ( B ) LOCATION: 5
        ( D ) OTHER INFORMATION: /note="Xaa at location 5 is
            fluorenylglycine"

( x i ) SEQUENCE DESCRIPTION: SEQ ID NO:29:

Tyr  Xaa  Leu  Arg  Xaa  Gly
  1                        5

( 2 ) INFORMATION FOR SEQ ID NO:30:

( i ) SEQUENCE CHARACTERISTICS:
        ( A ) LENGTH: 6 amino acids
        ( B ) TYPE: amino acid
        ( D ) TOPOLOGY: circular ( i i ) MOLECULE TYPE: peptide ( i x ) FEATURE:
        ( A ) NAME/KEY: Modified-site
        ( B ) LOCATION: 2
        ( D ) OTHER INFORMATION: /note="Xaa at location 2 is
            tryptophan in the D-configuration"

( i x ) FEATURE:
        ( A ) NAME/KEY: Modified-site
        ( B ) LOCATION: 5
        ( D ) OTHER INFORMATION: /note="Xaa at location 5 is
            fluorenylglycine"

( x i ) SEQUENCE DESCRIPTION: SEQ ID NO:30:

Tyr Xaa Leu Arg Xaa Gly
1               5

( 2 ) INFORMATION FOR SEQ ID NO:31:

( i ) SEQUENCE CHARACTERISTICS:
        ( A ) LENGTH: 6 amino acids
        ( B ) TYPE: amino acid
        ( D ) TOPOLOGY: circular ( i i ) MOLECULE TYPE: peptide ( i x ) FEATURE:
        ( A ) NAME/KEY: Modified-site
        ( B ) LOCATION: 2
        ( D ) OTHER INFORMATION: /note="Xaa at location 2 is
            tryptophan in the D-configuration"

( i x ) FEATURE:
        ( A ) NAME/KEY: Modified-site
        ( B ) LOCATION: 5
        ( D ) OTHER INFORMATION: /note="Xaa at location 5 is
            diphenylalanine"

( x i ) SEQUENCE DESCRIPTION: SEQ ID NO:31:

Tyr Xaa Leu Arg Xaa Gly
1               5

( 2 ) INFORMATION FOR SEQ ID NO:32:

( i ) SEQUENCE CHARACTERISTICS:
        ( A ) LENGTH: 6 amino acids
        ( B ) TYPE: amino acid
        ( D ) TOPOLOGY: circular ( i i ) MOLECULE TYPE: peptide ( i x ) FEATURE:
        ( A ) NAME/KEY: Modified-site
        ( B ) LOCATION: 2
        ( D ) OTHER INFORMATION: /note="Xaa at location 2 is
            tryptophan in the D-configuration"

( i x ) FEATURE:
        ( A ) NAME/KEY: Modified-site
        ( B ) LOCATION: 5
        ( D ) OTHER INFORMATION: /note="Xaa at location 5 is
            diphenylalanine"

( x i ) SEQUENCE DESCRIPTION: SEQ ID NO:32:

Tyr Xaa Leu Arg Xaa Gly
1               5

( 2 ) INFORMATION FOR SEQ ID NO:33:

( i ) SEQUENCE CHARACTERISTICS:
        ( A ) LENGTH: 6 amino acids
        ( B ) TYPE: amino acid
        ( D ) TOPOLOGY: circular ( i i ) MOLECULE TYPE: peptide ( i x ) FEATURE:
        ( A ) NAME/KEY: Modified-site
        ( B ) LOCATION: 2
        ( D ) OTHER INFORMATION: /note="Xaa at location 2 is
            tryptophan in the D-configuration"

( i x ) FEATURE:
        ( A ) NAME/KEY: Modified-site
        ( B ) LOCATION: 5
        ( D ) OTHER INFORMATION: /note="Xaa at location 5 is
            methyltyrosine"

( x i ) SEQUENCE DESCRIPTION: SEQ ID NO:33:

Tyr  Xaa  Leu  Arg  Xaa  Gly
1                   5

( 2 ) INFORMATION FOR SEQ ID NO:34:

( i ) SEQUENCE CHARACTERISTICS:
        ( A ) LENGTH: 6 amino acids
        ( B ) TYPE: amino acid
        ( D ) TOPOLOGY: circular ( i i ) MOLECULE TYPE: peptide ( i x ) FEATURE:
        ( A ) NAME/KEY: Modified-site
        ( B ) LOCATION: 2
        ( D ) OTHER INFORMATION: /note="Xaa at location 2 is
            tryptophan in the D-configuration"

( i x ) FEATURE:
        ( A ) NAME/KEY: Modified-site
        ( B ) LOCATION: 5
        ( D ) OTHER INFORMATION: /note="Xaa at location 5 is
            1,2,3,4- tetrahydroisoquinoline-3-carboxylic acid"

( x i ) SEQUENCE DESCRIPTION: SEQ ID NO:34:

Tyr  Xaa  Leu  Arg  Xaa  Gly
1                   5

( 2 ) INFORMATION FOR SEQ ID NO:35:

( i ) SEQUENCE CHARACTERISTICS:
        ( A ) LENGTH: 6 amino acids
        ( B ) TYPE: amino acid
        ( D ) TOPOLOGY: circular ( i i ) MOLECULE TYPE: peptide ( i x ) FEATURE:
        ( A ) NAME/KEY: Modified-site
        ( B ) LOCATION: 2
        ( D ) OTHER INFORMATION: /note="Xaa at location 2 is
            tryptophan in the D-configuration"

( i x ) FEATURE:
        ( A ) NAME/KEY: Modified-site
        ( B ) LOCATION: 5
        ( D ) OTHER INFORMATION: /note="Xaa at location 5 is
            1,2,3,4- tetrahydroisoquinoline-3-carboxylic acid
            in the D- configuration"

( x i ) SEQUENCE DESCRIPTION: SEQ ID NO:35:

Tyr  Xaa  Leu  Arg  Xaa  Gly
1                   5

( 2 ) INFORMATION FOR SEQ ID NO:36:

( i ) SEQUENCE CHARACTERISTICS:
        ( A ) LENGTH: 6 amino acids
        ( B ) TYPE: amino acid
        ( D ) TOPOLOGY: circular ( i i ) MOLECULE TYPE: peptide ( i x ) FEATURE:
        ( A ) NAME/KEY: Modified-site
        ( B ) LOCATION: 2
        ( D ) OTHER INFORMATION: /note="Xaa at location 2 is
            tryptophan in the D-configuration"

( i x ) FEATURE:
        ( A ) NAME/KEY: Modified-site
        ( B ) LOCATION: 5

(D) OTHER INFORMATION: /note="Xaa at location 5 is 1,2,3,4- tetrahydroisoquinoline-7-hydroxy-3-carboxylic acid"

(xi) SEQUENCE DESCRIPTION: SEQ ID NO:36:

Tyr Xaa Leu Arg Xaa Gly
1               5